United States Patent
Antony

(10) Patent No.: US 11,241,472 B2
(45) Date of Patent: Feb. 8, 2022

(54) PHARMACEUTICAL COMPOSITION MADE FROM HYDROPHOBIC PHYTOCHEMICALS DISPERSED IN SESAME OIL TO ENHANCE BIOACTIVITY

(71) Applicant: Benny Antony, Aluva (IN)

(72) Inventor: Benny Antony, Aluva (IN)

(73) Assignee: Arjuna Natural Pvt. Ltd., Kerala (IN)

( * ) Notice: Subject to any disclaimer, the term of this patent is extended or adjusted under 35 U.S.C. 154(b) by 0 days.

(21) Appl. No.: 16/763,945

(22) PCT Filed: Nov. 14, 2018

(86) PCT No.: PCT/IB2018/058948
§ 371 (c)(1),
(2) Date: May 13, 2020

(87) PCT Pub. No.: WO2019/097417
PCT Pub. Date: May 23, 2019

(65) Prior Publication Data
US 2020/0384060 A1 Dec. 10, 2020

(30) Foreign Application Priority Data
Nov. 14, 2017 (IN) .............................. 201741040560

(51) Int. Cl.
*A61K 36/324* (2006.01)
*A61K 36/9066* (2006.01)
*A61P 29/00* (2006.01)
*A61K 31/12* (2006.01)
*A61K 47/44* (2017.01)

(52) U.S. Cl.
CPC .......... *A61K 36/9066* (2013.01); *A61K 31/12* (2013.01); *A61K 36/324* (2013.01); *A61K 47/44* (2013.01); *A61P 29/00* (2018.01)

(58) Field of Classification Search
None
See application file for complete search history.

(56) References Cited

U.S. PATENT DOCUMENTS

| | | | |
|---|---|---|---|
| 6,589,516 B1 * | 7/2003 | Eyre | A61Q 5/00 424/70.1 |
| 7,883,728 B2 | 2/2011 | Antony | |
| 2005/0100622 A1 | 5/2005 | Nair et al. | |
| 2007/0218187 A1 | 9/2007 | Miyake et al. | |
| 2013/0084348 A1 | 4/2013 | Gokaraju et al. | |
| 2014/0039031 A1 * | 2/2014 | Brough | A61K 31/05 514/414 |
| 2014/0080916 A1 | 3/2014 | Rishton et al. | |
| 2015/0152056 A1 | 6/2015 | Rawat et al. | |
| 2016/0113990 A1 * | 4/2016 | Cockburn | A61K 2300/00 424/756 |
| 2016/0136214 A1 * | 5/2016 | Parthasarathy | A61K 36/185 424/776 |
| 2017/0112823 A1 * | 4/2017 | Nigam | A61K 31/185 |
| 2019/0255138 A1 * | 8/2019 | Antony | A61K 36/185 |

FOREIGN PATENT DOCUMENTS

| | | | |
|---|---|---|---|
| EP | 2229940 A1 | | 9/2010 |
| IN | 2171/DEL/2009 | * | 7/2016 |
| WO | 2016062402 A1 | | 4/2016 |
| WO | 2017068600 A1 | | 4/2017 |

OTHER PUBLICATIONS

Mahdizadeh, S. et al. Avicenna's Canon of Medicine: A Review of Analgesics and Anti-Inflammatory Substances. Avicenna J of Phytomedicine 5(3)182-202, May 2015. (Year: 2015).*
Rudrappa, G. et al. Efficacy of High Dissolution Tumeric Sesame Formulation for Pain Relief in Adult Subjects . . . Medicine 99(28)1-8, 2020. (Year: 2020).*
Singh, M. et al. Potential Analgesic and Anti-Pyretic Herbal Drugs. Int J of Phytomedicine 2(3)197-209, 2010. (Year: 2010).*
Examination Report issued in corresponding Indian Application No. 201741040560 dated Mar. 29, 2021.
Key Attributes of TKDL; <http://www.tkdl.res.in/tkdl/LangDefault/Formulation/Demo_Docs/BC/unani/highlight.asp?a=/tkdl/langdefault/formulation/demo_docs/bc/unani/na2-217.asp&b=boswellia&c=F&stypePrint=GLOBAL-SIMPLE-SEARCH?str=Global>, retrieved May 4, 2021.
PCT/IB2018/058948 International Search Report completed Apr. 23, 2019.
PCT/IB2018/058948 Written Opinion completed Apr. 23, 2019.
Sharma et al. "Essential Oils of *Curcuma longa* L. from Bhutan" Journal of Essential Oil Research, 1997; 9(5):589-592 (doi: 10.1080/10412905.1997.9700783).
EuroPharma USA "Curamin" Released no later than 2014 (per ISR. Retrieved May 13, 2020 (https://www.europharmausa.com/products/curamin/).
Fresh Nutrition "Organic Turmeric Curcumin with Added Boswellia & Bioperine for Potent Joint & Inflammation Support—Best" Released no later than Oct. 23, 2017 (per ISR). Retrieved May 13, 2020 (https://www.amazon.com/Turmeric-Curcumin-Boswellia-Bioperine-Inflammation/dp/B01N4WCQNM).

* cited by examiner

*Primary Examiner* — Ralph J Gitomer
(74) *Attorney, Agent, or Firm* — Venable LLP; Keith G. Haddaway; Daniel M. Podgorksi

(57) ABSTRACT

Pharmaceutical formulations and methods to increase the bioactivity and bioavailability of plant compound having hydrophobic phytochemicals which have poor bioavailability due to poor water solubility. Dispersions of extracts of *Boswellia* and/or *Curcuma longa* in sesame seed oil. Analgesic and anti-inflammatory composition having a) an extract of *Boswellia*, b) one or more of an extract of *Curcuma longa*, a curcuminoid composition and combinations thereof, and, c) a sesame seed oil. The analgesic and anti-inflammatory composition has particles having a particle size ranging from less than about 20 micrometers to about 1 micrometer. The analgesic and anti-inflammatory composition provides a total combined specific surface area provided by particles in the composition ranging from about 900 meter$^2$ per kilogram to about 3000 meter$^2$ per kilogram of the composition. Methods of preparing the compositions and methods of treating inflammation and musculoskeletal disorders are provided.

13 Claims, 10 Drawing Sheets

(a)

(b)

(a)

(b)

PHARMACEUTICAL COMPOSITION MADE FROM HYDROPHOBIC PHYTOCHEMICALS DISPERSED IN SESAME OIL TO ENHANCE BIOACTIVITY

This application is a U.S. National Phase of PCT/IB2018/058948, filed Nov. 14, 2018, which claims priority from IN 201741040560, filed Nov. 14, 21017. All of which is incorporated by reference in its entirety.

FIELD

The disclosure relates to nano-particle dispersion in oil, such as formulation made from hydrophobic phytochemicals dispersed in sesame oil to enhance bioactivity. The formulation is standardized into a specific formulation, product and dosage. The formulation can be used in natural dietary and health supplementation. The disclosure also relates to a method to increase bioavailability of water-insoluble plant compounds. The disclosure also relates to a method of manufacturing the formulation and use of the product in the treatment of chronic inflammation, arthritis, crohn's disease, asthma, osteoarthritis, lupus, rheumatoid arthritis, and inflammatory bowel disease.

BACKGROUND

Herbal products are more often linked to health and recommended as health supplements. These herbal products more often derive their root from traditional medicines, but unlike traditional medicines modern herbal products are tested against modern medicines. Active phytochemicals are being identified, standardized and new products are being developed. Phytochemicals are gaining popularity because of having fewer side effects. But unlike synthetic drugs, herbal products have poor bioavailability and, therefore, the dosage required for medicinal formulation is much higher.

When drugs are administered orally, it passes through multiple barriers before it can reach the bloodstream and this lead to drug wastage. The proportions of drug that make it to the bloodstream on oral administration determine the bioavailability of drugs. Bioavailability of drugs determines its dosage and applicability.

Among the phytochemicals, some are lipid soluble and some water-soluble, and the latter has a greater likelihood of making it to the systemic circulation. Sometimes the lipid soluble or hydrophobic phytochemicals have advanced potency but because of poor bioavailability fails to deliver. Higher dosage is required in case of phytochemicals with poor bioavailability because of drug wastage.

There are many ways to increase the bioavailability of phytochemicals. According to U.S. Pat. No. 7,883,728B2, bioavailability of curcumin is enhanced by linking the curcuminoids with Ar-turmerone, and the formulation produced a synergetic effect.

In US 2013/0084348A1 the non-polar *Boswellia* extract is used as bio-enhancing agents for biological agents such as amino acid, nutrients, vitamins. *Boswellia* extract has its own activity, *Boswellia* acid derived from *Boswellia* has anti-inflammatory activity. Boswellic acids seem to be specific inhibitor of 5-LO, which is one of the enzyme that is responsible for inflammation.

In WO2017068600 A1 the bioavailability of withanolide glycosides and saponins derived from *Withania somnifera* is enhanced by delivering them directly in intestine and avoiding release in stomach altogether. Providing enteric coating or sustained release is one of the methods to increase the bioavailability and bioactivity of a drug, or compounds derived from plant.

One method of improving bioavailability of drugs is by reducing the particle size of the plant derivatives. As the partial size reduces there are significant changes in the property is observed. A particle at nano-scale is made up of fewer molecules which results in high energy gap, which can be a reason for improvement in the bioavailability.

One method of improving bioavailability of drugs is by reducing the particle size of the plant derivatives. As the particle size reduces there are significant changes in the property is observed. A particle at nano-scale is made up of fewer molecules which results in high energy gap, which can be a reason for improvement in the bioavailability. Another reason is the increased surface are that increases the reaction area enabling it to be absorbed in to blood.

Sesame oil, *Boswellia* extract and cucuminoids all have some level of analgesic or anti-inflammatory property, but not particularly uses the same mechanism to inhibit pain and inflammation. A combination of the three can provide a comprehensive action against pain and inflammation especially in inhibiting lipoxygenase, cyclooxygenase or NF-kB. Sesame oil being a lipid can be used as a carrier medium but only 2% of *Boswellia* extract and curcuminoid mixture can be loaded in to sesame oil. A method is required to load more *Boswellia* extract or curcuminoids in to sesame oil and obtain a stable product where the loaded extracts do not precipitates or settle down.

Objectives

The primary objective is to enhance bioavailability of phytochemicals with poor bioavailability and is poorly water-soluble or hydrophobic in nature.

Another objective is to have a formulation with nano-scale or micro-scale plant particles stabilised by dispersing uniformly in an oil to improve bioactivity and bioavailability.

One more objective is to develop a method to make dispersion with micro to nano-particle size active ingredients dispersed in it. Yet another objective is to develop a method to manufacture a bioactive formulation and composition.

SUMMARY

Analgesic and anti-inflammatory composition having a) an extract of *Boswellia*, b) one or more of an extract of *Curcuma longa*, a curcuminoid composition and combinations thereof, and, c) a sesame seed oil is disclosed. The particles of extract of *Boswellia* and extract of *Curcuma longa* or a curcuminoid composition are dispersed in sesame oil. The particle size ranges from less than about 20 micrometre to about 1 micrometre. The analgesic and anti-inflammatory composition provides a total combined specific surface area provided by particles in the composition. The total combined surface area of the particles in the composition ranges from about 900 meter$^2$ per kilogram to about 3000 meter$^2$ per kilogram of the composition. The particle can have components a), b), a combination of a) and b), or combinations thereof.

An anti-inflammatory and anti-analgesic composition of a) an extract of *Boswellia*, b) one or more of an extract of *Curcuma longa*, a curcuminoid composition and combinations thereof, and, c) a sesame seed oil, where the composition is in the form of a dispersion is provided. The dispersion has particles. The particles can have components a), b), a combination of a) and b), or combinations thereof.

In some embodiments of the analgesic and anti-inflammatory composition, the particle size of the particle ranges from less than about 20 micrometers to about 1 micrometer.

In some embodiments a dosage form of the analgesic and anti-inflammatory composition is provided. The composition in the dosage form is in the form of a dispersion having particles. About 50% of the particles in the dosage form of the composition have a particle size of less than about 5 micrometer.

In some embodiments, a weight ratio of components a):b):c) ranges from about 1:1:1 to about 5:1:99. In some embodiments, a weight ratio of components a):b):c) is about 3:1:6.

In some embodiments, the sesame seed oil includes about 30% to about 70% sesame lignans. In some embodiments, the sesame lignans are in a weight ratio of sesamin:sesamolin of about 1:1.

The extract of Boswellia in the anti-inflammatory and anti-analgesic composition includes about 1% to about 30% acetyl-11-keto-beta-boswellic acid. In some embodiments, the extract of Boswellia includes about 10% acetyl-11-keto-beta-boswellic acid.

The curcuminoid composition in the anti-inflammatory and anti-analgesic composition includes a curcuminoid mixture and an essential oil of turmeric. The curcuminoid composition includes curcumin, demethoxycurcumin and bisdemethoxycurcumin. In some embodiments, the essential oil of turmeric includes at least about 15% ar-turmerone. In some embodiments, the essential oil of turmeric includes about 40 to about 50% ar-turmerone. In some embodiments, the essential oil of turmeric includes at least about 15% alpha turmerone.

A dosage form of the anti-inflammatory and anti-analgesic composition is provided. The dosage form can be hard gel capsule, soft gel capsule, paste, ointment, infusion, injection, ampoule, solution, suspension, emulsion, oil or cream.

A method of treating inflammation in a subject in need thereof is provided. The method includes administering an effective amount of the analgesic and anti-inflammatory composition.

The method includes administering an effective amount of the analgesic and anti-inflammatory composition. The subject is treated for conditions such as low back pain, general whole body pain, myalgia, headache, neck pain, limb pain, grade one sprain, joint pain, acute soft tissue injury, acute injuries of ligaments and acute injuries of tendons. The method of treatment includes inhibiting one or more of lipoxygenase, cyclooxygenase and NF-kB. Methods of treatment include administering the analgesic and anti-inflammatory composition whereby a Numerical Rating Scale shows an improvement of about 70% in about 6 hours after administering the composition. In some embodiments, the Numerical Rating Scale shows an improvement of about over 80% after administering the composition every day for 7 days. In some embodiments of the method of treatment, a Pain Relief Scale (PRS) improves about 75% in about 6 hours after administration the composition. In some embodiments of the method of treatment, a Pain Relief Scale improves about 75% after administering the composition for 7 days. In some embodiments of the method of treatment, Meaningful Pain Relief is observed within 5 min after administering the composition.

Methods of preparing an analgesic and anti-inflammatory composition are provided. The composition includes a) an extract of Boswellia, b) one or more of an extract of Curcuma longa, a curcuminoid composition and combinations thereof, and, c) a sesame oil. The method or preparation includes mixing a), b) and c) to obtain a mixture. The composition is subjected to milling, and repeating the milling of the composition several times till the particle size is as required. The particles have a particle size ranging from less than about 20 micrometre to about 1 micrometre. The total combined surface area provided of particles in the composition ranges from about 900 meter$^2$ per kilogram to about 3000 meter$^2$ per kilogram of the composition. The particle can have components a), b), a combination of a) and b), or combinations thereof.

An analgesic and anti-inflammatory composition having an extract of Boswellia, and, a sesame oil is provided. The particles of extract of Boswellia are dispersed in sesame oil The particles having a particle size ranging from less than about 20 micrometre to about 1 micrometre. The analgesic and anti-inflammatory composition provides a total combined specific surface area provided by particles in the composition. The total combined surface area of the particles in the composition ranges from about 900 meter$^2$ per kilogram to about 3000 meter$^2$ per kilogram of the composition.

Disclosure provides an extract of Boswellia and methods of preparing the same. The extract of Boswellia includes about 10% acetyl-11-keto-beta-boswellic acid and less than about 0.1% 11-keto-beta-boswellic acid. The method includes steam distilling gum resin pellets of Boswellia mixed with water. Then essential oil from the steam distillation is collected. The water from the steam distillation is drained to obtain a first gummy residue. The first gummy residue is extracted with ethyl acetate at about 70° C. to obtain a second residue and a first supernatant. A liquid-liquid extraction of the first supernatant is performed by adding sodium hydroxide dissolved in first supernatant, water soluble part get extracted from first supernatant to water. Hydrochloric acid is added to the water soluble phase to obtain a precipitate and a second supernatant. The precipitate is dried and pulverized to obtain a powder. The powder is the extract of Boswellia having about 10% acetyl-11-keto-beta-boswellic acid and about 0.1% to about 0.3% 11-keto-beta-boswellic acid.

Methods for further enriching the 10% acetyl-11-keto-beta-boswellic acid to about 70%, the method are provided. The method includes a) dissolving the extract of Boswellia having about 10% acetyl-11-keto-beta-boswellic acid and about 0.1% to about 0.3% 11-keto-beta-boswellic acid in ethyl acetate to obtain a solution. The solution is loaded onto a silica column. The silica column is extracted with hexane to obtain a first elute and a first eluted column. The first eluted column is extracted with a solvent having hexane and ethyl acetate in a ratio of about 95:5 to obtain a second elute and a second eluted column. The second elute includes about 80% beta boswellic acid and about 20% alpha boswellic acid. The second eluted column is eluted with a solvent having hexane and ethyl acetate in a ratio of about 90:10 to obtain a third elute and a third eluted column. The third elute includes beta-boswellic acid, alpha boswellic acid and 3-O-acetyl boswellic acid. The third eluted column is extracted with a solvent having hexane and ethyl acetate in a ratio of about 80:20 to obtain a fourth elute and a fourth eluted column. The fourth elute includes alpha boswellic acid, 3-O-acetyl boswellic acid and acetyl-11-keto-beta-boswellic acid. The fourth eluted column is eluded with a solvent having hexane and ethyl acetate in a ratio of about 70:30 to obtain a fifth elute and a fifth eluted column. The fifth elute includes about 70% acetyl-11-keto-beta-boswellic acid and about 30% 11-keto-beta-boswellic acid. The fifth eluted column is extracted with a solvent having hexane and ethyl acetate in a ratio of about 60:40 to obtain a sixth elute and a sixth eluted column. The sixth elute includes about 10% acetyl-11-keto-beta-boswellic acid and 11-keto-beta-boswellic acid. The sixth eluted column is extracted with a solvent having hexane and ethyl acetate in a ratio of about 20:80 to obtain a seventh elute a seventh eluted column. The seventh eluted column is eluted with ethyl acetate to obtain an eighth elute. The extract of *Boswellia* is any one of the first elute, the second elute, the third elute, the fourth elute, the fifth elute, the sixth elute, the seventh elute, the eighth elute, or combinations thereof.

Disclosure provides a uniform blend composition having an extract of *Boswellia* and sesame oil and methods of preparing the same. The method includes mixing sesame oil and the extract of *Boswellia* to obtain a mixture. Subjecting the mixture to milling repeatedly to obtain a uniform blend composition whereby the uniform blend composition has a particle having a surface area ranging from about 900 to about 3000 meter$^2$ per kilogram.

An anti-inflammatory composition having an extract of *Curcuma longa*, a curcuminoid composition and combinations thereof, and sesame oil is disclosed. The anti-inflammatory composition has particles having a particle size ranging from less than about 20 micrometre to about 1 micrometre. The total combined surface area of particles in the composition ranges from about 900 meter per kilogram to about 3000 meter per kilogram of the composition. Methods of preparing the composition include mixing a) and b) to obtain a mixture, subjecting the mixture to milling to obtain a homogenised blend of the composition.

BRIEF DESCRIPTION OF THE DRAWINGS

The above objectives and advantages of the disclosed teachings will become more apparent by describing in detail embodiments thereof with reference to the attached drawings in which.

DETAILED DESCRIPTION

Figure 1:
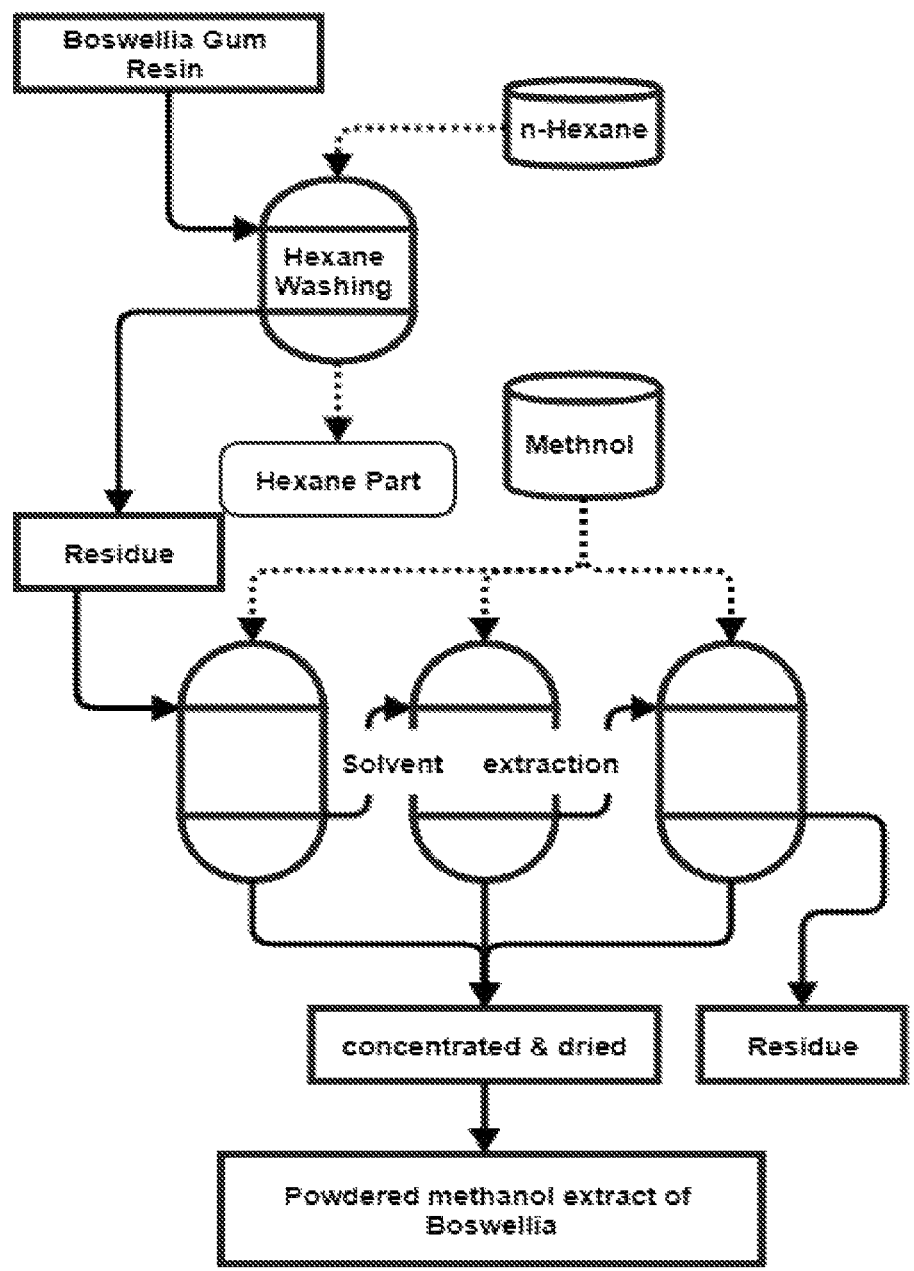
FIG. 1: Method of obtaining *Boswellia* extract using methanol.

Medicinal compositions are disclosed. Also disclosed are methods to enhance bioactivity of hydrophobic phytochemicals and the process to make them. The formulation and its features are disclosed hereon through various embodiments.

Each embodiment describes a novel feature. Some embodiments have multiple aspects and such aspects provide the scope of the embodiments. Through the following embodiments, a formulation and product along with a process of manufacturing and method of use is disclosed. The embodiments have to be understood in its broadest sense.

The source of plant compounds disclosed throughout the specification can be any one or a combination of an extract, juice, lyophilized juice powder, dried plant part power, pulp, flakes and raw plant parts.

All the ratios and proportions of blends, mixtures and combinations are in weight bases and are to be taken in weight bases if not specified otherwise.

Boswellic acid or *Boswellia* acid may be used interchangeably throughout the specification. The Boswellic acid primarily has Acetyl-11-keto-beta-boswellic acid (AKBA), 11-keto-β-boswellic acid (KBA), β-boswellic acid (β-BA), α-boswellic acid (α-BA), and acetyl-α-boswellic acid (AαBA).

Standard extract of *Boswellia* as described in the specification includes solvent extract of *Boswellia* frankincense (resin) or just *Boswellia* oil extracted using supercritical $CO_2$ extract. In such *Boswellia* extracts the AKBA might be or might not be standardized. AKBA is not the prevalent boswellic acid in *Boswellia* frankincense, without any special enrichment the AKBA content in *Boswellia* extract may stay below 5%.

The minimum particle size of powdered plant extracts goes close to 100 μm and an average particle size of roughly 400 μm and more. The specific surface area (SSA) of such extract is below 200 m$^2$/Kg.

The specific surface area (SSA) is total surface area of a material per unit of mass, powdered and granules have high surface area compared to a solid block or a chunk of the same weight. Increased surface area means increased reaction area, making a drug more active than normal. At the same time increased surface area also means the risk of agglomeration of particles. Increasing SSA enhances the bioavailability of the active components. By loading high concentration of the plant extract into oils such as sesame seed oil agglomeration can be avoided. In the present application the active components are the plant extract or extract composition. Plant extracts particle in micro or nano scale cannot be administered directly, it needs a carrier or it will result in agglomeration. Sesame oil keeps the high energy micro or nano-particles stable and it also acts as a carrier. The compounds with SSA of 3000 m$^2$/Kg the partial size of such compounds can go down to nano scale.

Hydrophobic plant compounds have poor bioavailability because of their poor dissolution rate. Enhancing the bioavailability will reduce drug wastage and improve the activity of compounds derived from plants. It was observed that a uniformly dispersed plant compound in sesame oil is more active than using plant compound as such. The plant compounds were dispersed in other desolation mediums also such as coconut oil, olive oil and rice bran oil but the best results were obtained with sesame seed oil.

Studies conducted by the inventor revealed that reduced size enabled higher concentration of plant extracts to be dispersed or loaded in to oil. The inventor also found that such formulation made with *Boswellia* extract loaded in sesame oil has a greater bioavailability and faster activity compared to *Boswellia* extract per se. A notable improvement was seen in a formulation made of curcuminoid compound, water insoluble *Boswellia* extract and sesame lignans dispersed uniformly in a lipid solvent. The average SSA for the formulation was about 3000 m$^2$/Kg. Plant extracts which generally form a colloidal with sesame oil are uniformly dispersed when particle size is reduced. The formulation was tested for activity alongside a mixture of curcuminoid compound, water insoluble *Boswellia* extract and sesame lignans dissolved in a lipid solvent with a SSA of less than 200 m$^2$/Kg.

Sesame seed oil is bioactive oil and has multiple therapeutic benefits, but in the disclosed embodiments, sesame oil is used as a carrier to enhance the bioavailability of plant extracts with poor water solubility. It was observed that plant extract dispersed in sesame oil has a higher bioactivity and bioavailability compared to their counterpart. A dispersion of plant extract in sesame oil had an efficacy greater than theoretically expected values, which signifies a synergy.

Activity of *Boswellia*, more specifically activity of boswellic acid such as AKBA is improved by dispersing *Boswellia* extract in oil, specifically in sesame oil. Blending with sesamin oil avoids the fast metabolic reduction of AKBA but simple addition *Boswellia* into oil such as sesamin oil do not make a perfect homogenized solution, it rather become a thick colloidal. Blending should be done in or below micron scale to get desired results. The desired result is a uniformly suspended *Boswellia* acid in sesame oil.

Some embodiments also enriched AKBA in *Boswellia* extract. *Boswellia* extract is obtained from *Boswellia* gum resin through solvent extraction. The oil part of the resin can be removed by hexane washing or by distillation. There are many ways of making an AKBA rich *Boswellia* extract, such as introducing an acetyl group into *Boswellia* extract is one of the most common methods of producing AKBA from boswellic acid. AKBA can be enriched without alkylation using silica gel column chromatography.

An analgesic and anti-inflammatory composition is provided. The composition includes a) an extract of *Boswellia*, b) one or more of an extract of *Curcuma longa*, a curcuminoid composition and combinations thereof, and, c) a sesame seed oil. The weight ratio of a):b):c) ranges from about 1:1:1 to about 5:1:99. The above composition is made of 30±5% *Boswellia* extract, 10±5% extract of *Curcuma longa* or curcuminoid composition and 60±5% sesame oil by weight. The composition is a homogenised dispersion of *Boswellia* extract and turmeric extract in sesame oil. In other words at least a 40% loading of solid *Boswellia* extract, turmeric extract in sesame oil.

In some embodiments, a weight ratio of a):b):c) is about 3:1:6. The proportion of each component in the composition; *Boswellia* extract and extract of *Curcuma longa* or curcuminoid composition are in 1:1 to 5:1 ratio, preferably 3:1 by weight. The *Boswellia* extract and extract of *Curcuma longa* or curcuminoid composition to sesame oil are in 1:1 to 1:99 ratio, more preferably 1:1 to 1:10 by weight. Some other preferred ratios are 2:3, 5:7 and 11:19.

The composition is a dispersion of micro scale or nanoparticles of *Boswellia* extract, *Curcuma longa*, a curcuminoid composition and combinations in sesame oil. The plant extracts are dispersed uniformly in the oil to make it a homogenised solution. The analgesic and anti-inflammatory composition has particles having a particle size ranging from less than about 20 micrometers to about 1 micrometer. The analgesic and anti-inflammatory composition provides a total combined specific surface area provided by particles in the composition. The total combined surface area provided by particles in the composition ranges from about 900 meter$^2$ per kilogram to about 3000 meter$^2$ per kilogram of the composition. The particle can have components a), b), a combination of a) and b), or combinations thereof.

In the analgesic and anti-inflammatory composition the *Boswellia* extract and extract of *Curcuma longa* or curcuminoid composition have a specific-surface-area (SSA) of more than 900 m$^2$/Kg more preferably above 3000 m$^2$/Kg. The SSA of the *Boswellia* extract and turmeric extract dispersed in lipid solution is 5 to 15 fold greater than regular *Boswellia* extract, more precisely 9 to 12 fold. The average particle size of dispersed *Boswellia* extract and turmeric extract is less than 20 μm-1 μm, more precisely about 50% of particles have a particle size less than 5 μm.

In some embodiments, the sesame seed oil includes about 30% to about 70% sesame lignans. In some embodiments, the sesame lignans are in a weight ratio of sesamin to sesamolin is 1:1.

In some embodiments the *Boswellia* extract in the composition is preferably a water-insoluble *Boswellia* extract made of over 30% boswellic acid, more precisely at least 10% AKBA, less than 1% KBA, 5-12% α-BA and 19-28% β-BA. The curcuminoid composition is made of combination of curcuminoids and essential oil of turmeric. The essential oil of turmeric comprises ar-turmerone at least 15% by weight or α-turmerone at least 15% by weight or both. The composition is a homogenised dispersion of Water-insoluble *Boswellia* extract and curcuminoid composition in sesame oil.

A dosage form of the anti-inflammatory and anti-analgesic composition is provided. The dosage form can be hard gel capsule, soft gel capsule, paste, ointment, infusion, injection, ampoule, solution, suspension, emulsion, oil or cream. The composition could be administered to human beings at a dose of 50 mg to about 2000 mg. About 50% of the particles in the dosage form of the composition have a particle size of less than about 5 micrometre A method of treating inflammation in a subject in need thereof is provided. The method includes administering an effective amount of the analgesic and anti-inflammatory composition.

A method of treating inflammation and muscular skeletal pain in a subject in need thereof is provided. The method includes administering an effective amount of the analgesic and anti-inflammatory composition. The subject is treated for conditions such as low back pain, general whole body pain, myalgia, headache, neck pain, limb pain, grade one sprain, joint pain, acute soft tissue injury, acute injuries of ligaments and acute injuries of tendons.

Methods of treatment include administering the analgesic and anti-inflammatory composition whereby a Numerical Rating Scale shows an improvement of about 70% in about 6 hours after administering the composition.

In some embodiments, the Numerical Rating Scale shows an improvement of about over 80% after administering the composition every day for 7 days. In some embodiments of the method of treatment, a Pain Relief Scale (PRS) improves about 75% in about 6 hours after administration the composition. In some embodiments of the method of treatment, a Pain Relief Scale improves about 75% after administering the composition for 7 days. In some embodiments of the method of treatment, Meaningful Pain Relief is observed within 5 min after administering the composition.

The method of treatment includes inhibiting one or more of lipoxygenase, cyclooxygenase and NF-kB.

In some embodiment a powdered extract of *Boswellia* is disclosed, where the ratio between AKBA to KBA is manipulated and fixed at 90:1 to 1:1, the ratio between AKBA to β-BA is fixed at 90:1 to 1:1. A much more preferred ratio of AKBA to KBA will be 50:1 to 1:1 and more preferably 30:1 to 10:1 and most preferably 20:1 to 10:1. A much more preferred ratio of AKBA to β-BA is 50:1 to 1:1 and more preferably 30:1 to 1:1 and most preferably 20:1 to 3:1.

In some embodiment an analgesic and anti-inflammatory composition made of *Boswellia* extract and sesame oil is disclosed. The composition is a homogenised dispersion of *Boswellia* extract in sesame oil.

The proportion of each component in the composition; *Boswellia* extract to sesame oil is blended in 1:1 to 1:99 ratio, more preferably 1:1 to 1:10 by weight. Some other preferred ratios are 2:3, 5:7 or 11:19.

Another aspect of the embodiment, sesame lignans to boswellic acid are in a range of 3:5-1:100 ratios, more preferably 3:5-1:25, most preferably 2:5 ratio.

Yet another aspect of the embodiment, sesame lignans to AKBA are in a range of 1:4-1:90, more preferably 1:4 to 1:20 and most preferably 1:8 ratio.

Yet another aspect of the embodiment, sesamolin to AKBA is in a range of 1:10-1:90, more preferably 1:10-1:25 and most preferably 2:25 ratio.

Yet another aspect of the embodiment, sesamin to AKBA is in a range of 1:10-1:90, more preferably 1:10-1:35 and most preferably 1:25 ratio.

The *Boswellia* extract have a specific-surface-area (SSA) of more than $0.9 \times 10^3$ m$^2$/Kg more preferably above $3 \times 10^3$ m$^2$/Kg. The SSA of the *Boswellia* extract dispersed in lipid solution is 5 to 15 fold greater than regular *Boswellia* extract, more precisely 9 to 12 fold. The average particle size of dispersed *Boswellia* extract is less than 20µ-1µ, more precisely than 50% of dispersion has a particle size less than 5µ.

*Boswellia* extract is made of over 30% boswellic acid, more precisely at least 10% AKBA, less than 1% KBA, 5-12% α-BA and 19-28% β-BA. The *Boswellia* extract could be derived from solvent extract, supercritical extract, dried juice powder, or dried plant part.

Another aspect of the embodiment is a 100 mg dosage form of analgesic and anti-inflammatory composition. Table 1 provides the composition of 100 mg analgesic and anti-inflammatory composition.

TABLE 1

100 mg AKBA analgesic and anti-inflammatory composition

| Sesame oil | 56 mg | Sesaminol | 0.39 mg |
|---|---|---|---|
|  |  | Sesamin | 0.16 mg |
| *Boswellia* extract | 44 mg | AKBA | 4.4 mg |
|  |  | KBA | 0.18 mg |
|  |  | α-BA | 0.45 mg |
|  |  | B-BA | 1.16 mg |
|  |  | Total BA | 14.52 mg |

According to another aspect of the present embodiment, the composition is made into a dosage form for oral administration. The dosage form is selected from capsule, paste, ointment, infusion, injection, ampoule, solution, suspension, emulsion, oil, or, cream. The composition is administrable to human beings at a dose of 50 mg to about 2000 mg.

In some embodiment an analgesic and anti-inflammatory composition made of extract of *Curcuma longa* or curcuminoid composition and sesame oil. The composition is a homogenised dispersion of turmeric extract in sesame oil.

An aspect of the embodiment is the proportion of each component in the composition; extract of *Curcuma longa* or curcuminoid composition to sesame oil is blended in 1:1 to 1:99 ratio, more preferably 1:1 to 1:10 by weight. Some other preferred ratios are 2:3, 5:7 or 11:19.

Another aspect of the embodiment is that, the extract of *Curcuma longa* or curcuminoid composition have a specific-surface-area (SSA) of more than 900 m$^2$/Kg more preferably above 3000 m$^2$/Kg. The SSA of the extract of *Curcuma longa* or curcuminoid composition dispersed in lipid solution is 5 to 15 fold greater than regular *Boswellia* extract, more precisely 9 to 12 fold. The average particle size of dispersed *Boswellia* extract is less than 20µ-1µ, more precisely than 50% of dispersion has a particle size less than 5µ.

Another aspect of the embodiment is the curcuminoid composition; it is made of a combination of curcuminoids and essential oil of turmeric. The essential oil of turmeric comprises ar-turmerone at least 15% and α-turmerone at least 15%. The maximum limit for ar-turmerone and α-turmerone can go up to 50%.

According to another aspect of the present embodiment, the composition is made into a dosage form for oral administration. The dosage form is selected from capsule, sachet, paste, ointment, infusion, injection, ampoule, solution, suspension, emulsion, oil, or, cream. The composition is administrable to human beings at a dose of 50 mg to about 2000 mg.

In some embodiment a method to make the composition with water-insoluble *Boswellia* extract, extract of *Curcuma longa* or curcuminoid composition and sesame oil is disclosed. Said method comprises (refer to FIG. 6); (1) mixing *Boswellia* extract (powder) and curcuminoid composition (powder) in 3:1 ratio, (2) The mixture is blended with sesame oil in 2:3 ratio by weight, (3) Pass the 2:3 blend through a bead mill, (4) check for particle size of the blend and pass blend through bead mill till the average particle size of less than 5-2 µm is obtained. In some embodiment an anti-oxidant can also be added to improve the shelf life of the active components.

An aspect of the embodiment is water-insoluble *Boswellia* extract and curcuminoid composition. Water-insoluble *Boswellia* extract is made of over 30% boswellic acid, more precisely at least 10% AKBA, less than 1% KBA, 5-12% α-BA and 19-28% β-BA. Curcuminoid composition is made of combination of curcuminoids and essential oil of turmeric. The essential oil of turmeric comprises ar-turmerone at least 15% by weight or α-turmerone at least 15% by weight or both. The composition is a homogenised dispersion of Water-insoluble *Boswellia* extract and curcuminoid composition in sesame oil.

In some embodiment a method to make the composition with enhancing pain relief activity of water-insoluble *Boswellia* extract, and sesame oil is disclosed. Said method comprises (refer to FIG. 5); (1) mixing *Boswellia* extract (powder) and sesame oil in 2:3 ratio by weight, (2) Pass the 2:3 blend through a bead mill, (5) check for particle size of the blend and pass blend through bead mill till the average particle size of less than 5-2µ, is obtained. In some embodiment an anti-oxidant can also be added to improve the shelf life of the composition.

An aspect of the embodiment is water-insoluble *Boswellia* extract. Water-insoluble *Boswellia* extract is made of over 30% boswellic acid, more precisely at least 10% AKBA, less than 1% KBA, 5-12% α-BA and 19-28% β-BA. The composition is a homogenised dispersion of Water-insoluble *Boswellia* extract in sesame oil.

In some embodiment a process to make *Boswellia* extract with 10% AKBA comprises (Refer to FIGS. 2 and 3) is disclosed. Subject *Boswellia* frankincense to steam distillation, volatile oil is removed in the process. Water soluble part is removed when water used for distillation is filtered out leaving behind solid residue. The solid residue is subjected to Ethyl acetate to obtain a supernatant. NaOH added in the supernatant, then the supernatant is subjected to liquid-liquid extraction. The boswellic acid is converted to boswellic sales and the salt is dissolved in water. The water part and Ethyl acetate part is separated and water part is taken forwards. HCL is added to the water part and a precipitate is formed. The precipitate is dried to obtain *Boswellia* extract.

In some embodiment a process to enrich AKBA in *Boswellia* extract without acetylation. Powdered of *Boswellia* extract with 10% or less AKBA is mixed with ethyl acetate and blended with silica adsorbent. The ethyl acetate dried off and the silica gel is loaded into a preconditioned silica column. The column is initially eluted with Hexane and Hexane fraction is collected as Elute 1. Then the column is eluted with different ratio of Hexane and Ethyl acetate mixture:Elute 2—Hexane:Ethyl acetate 95:5; Elute 3—Hexane:Ethyl acetate 90:10; .Elute 4—Hexane:Ethyl acetate 80:20; Elute 5—Hexane:Ethyl acetate 70:30; Elute 6—Hexane:Ethyl acetate 60:40; and Elute 7—Hexane:Ethyl acetate 20:80. The column is finally eluted with 100% Ethyl acetate as Elute 8.

An elute for each mixture is collected (from Elute 2 to Elute 7), separated and tested for boswellic acids. The Elute 2 is the mixture of 80% beta boswellic acid and 20% alpha boswellic acid, elute 3 is the mixture of beta-boswellic acid, alpha boswellic acid and 3-O-acetyl boswellic acid, elute 4 is the mixture of, alpha boswellic acid, 3-O-acetyl boswellic acid and acetyl ketoboswellic acid (AKBA), elute 5 is the mixture of 70% acetyl ketoboswellic acid and 30% ketoboswellic acid, elute 6 is the mixture of 10% acetyl ketoboswellic acid. The Elutes are blended in such a manner to get a ratio of E1, E2 and E3:E1—is just Elute 5, (AKBA70%), E2—is a mix of Elute5 and Elute 4 (1:1) (AKBA60%), E3—is a mix of Elute5 and Elute 4(1:5) (AKBA50%).

FIG. 1 shows an extraction process to extract *Boswellia* extract for *Boswellia* gum resin. The *Boswellia* gum resin is loaded into a reaction chamber and to the reaction chamber required amount of n-Hexane is also added. The *Boswellia* resin is washed with the n-hexane in the chamber. The n-hexane part is filtered out and the reaming residue is taken forward. The residue is again loaded in to a reaction chamber and is extracted with methanol. The methanol part is filtered out and collected and the reaming residue is extracted two more time with fresh methanol in the same manner. All the methanol part are collected and concentrated under vacuum, the residue is discarded. The concentrate is dried to obtain a powdered menthol extract of *Boswellia* gum resin. The final product is also called the sample 3.

Figure 2:
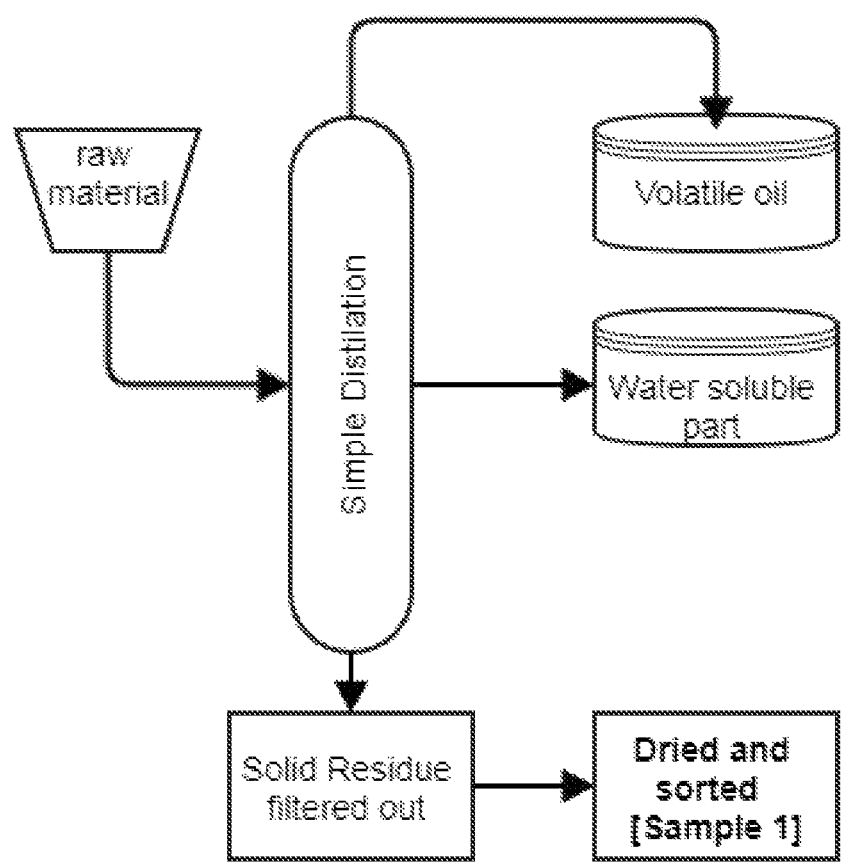
FIG. 2: Method of removing *Boswellia* oil from resin using steam distillation.

FIG. 2 shows steam distillation process of *Boswellia* gum resin. The raw material of the steam distillation is *Boswellia* gum resin. The raw material is fed in to the distillation unit. Through simple distillation the volatile is separated out from the top. After distillation the water in the distillation unit is drained out, water soluble part in the raw material is removed along with the drained water from the distillation unit. The remaining solid residue in the distillation unit is removed and dried. The dried residue is sample 1.

Figure 3:
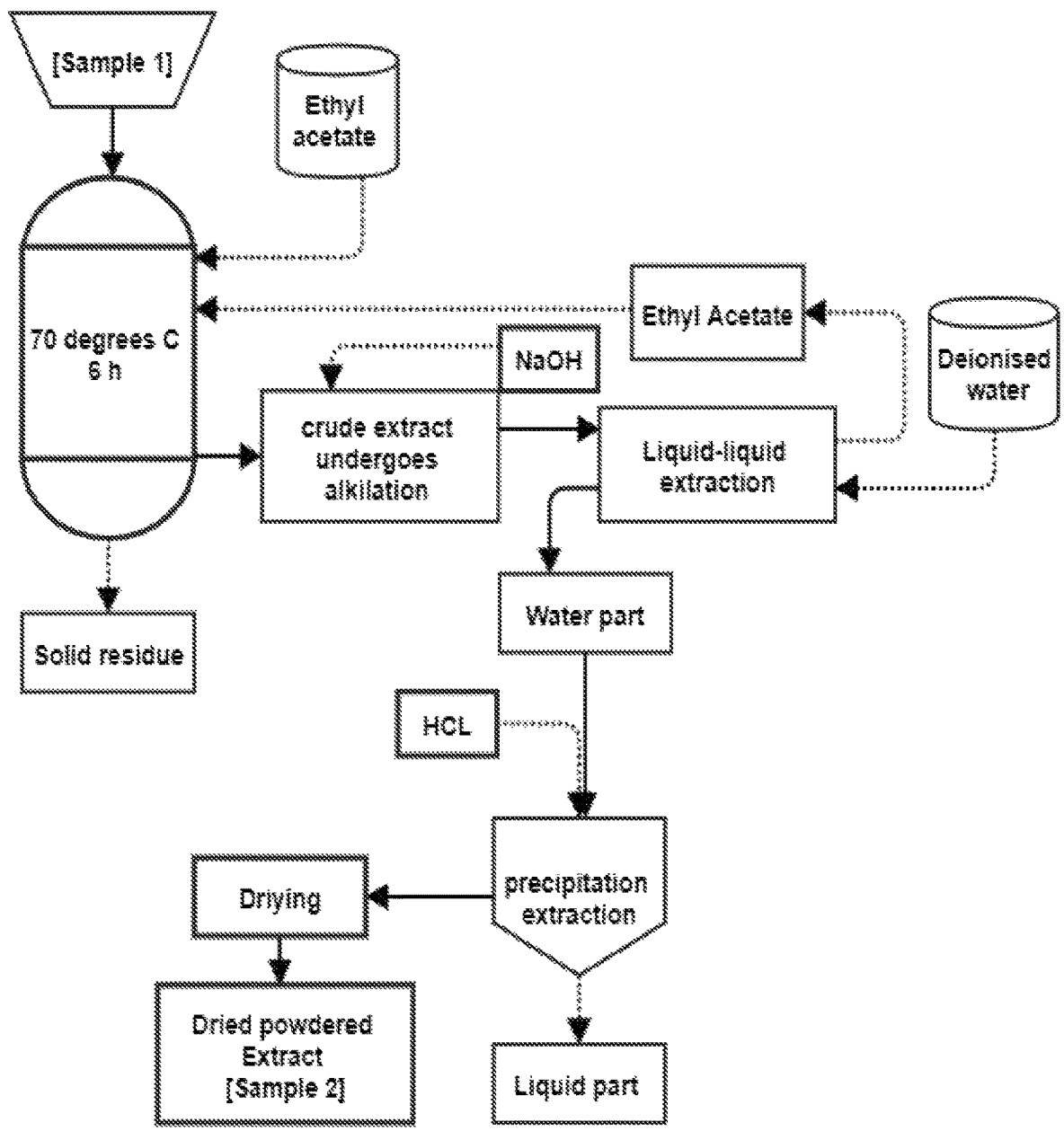
FIG. 3: Method of enriching AKBA in steam distilled *Boswellia* extract.

FIG. 3 Sample 1 is used as raw material, sample 1 is charged in to a reactor from the top. Ethyl acetate is also charged into the reactor. The Sample 1 is subjected to Ethyl acetate for 6 h at 70° C. After 6 h the Ethyl acetate part is removed and concentrated. In to the concentrate NaOH is added, this will result in the formation of Boswellic salts. The Ethyl acetate part is taken forward for a liquid-liquid extraction with water as other solvent. The Boswellic salts get extracted by the water and the water part is taken forward. The Ethyl acetate part after the liquid-liquid extraction is recycled to sample 1 reaction chamber. On to the water part adequate amount of HCL to for precipitate. The precipitate is removed and dried. The dried precipitate is the Ethyl acetate extract, also known as Sample 2.

Figure 4:
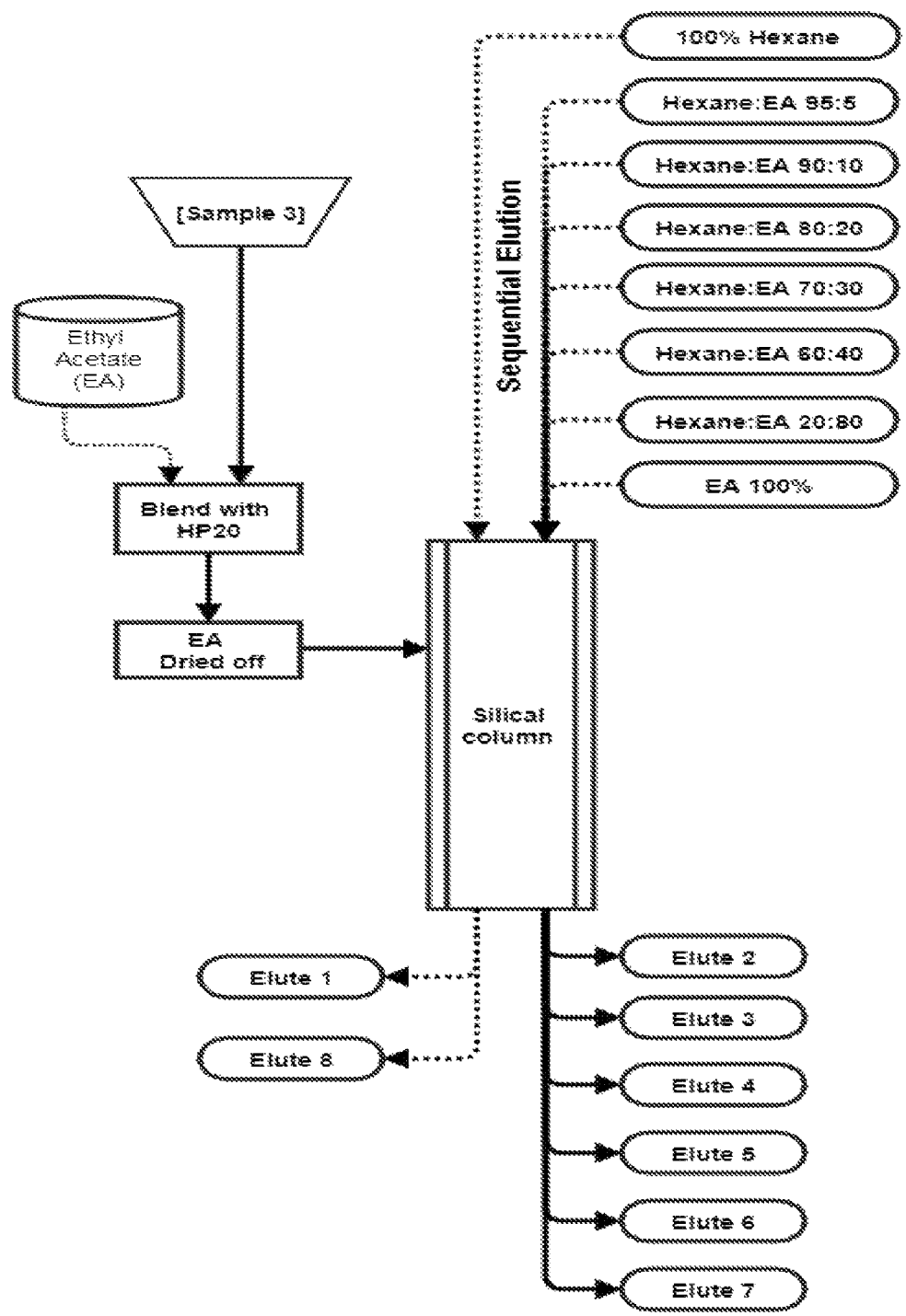
FIG. 4: Method to separate out AKBA from *Boswellia* extracts using Column chromatography.

FIG. 4 Sample 3 is dissolved in Ethyl acetate and mixed with HP 20 resin. Once mixed well the Ethyl acetate is dried off. The resin with Sample 3 is loaded on to a silica column. The column is first extracted with 100% Hexane, a elute 1 is obtained. Then with a mixture of hexane and ethyl acetate 95:5 ratio to obtain elute 2. Then with a mixture of hexane and ethyl acetate 90:10 ratio to obtain elute 3. Then with a mixture of hexane and ethyl acetate 80:20 ratio to obtain elute 4. Then with a mixture of hexane and ethyl acetate 80:20 ratio to obtain elute 5. Then with a mixture of hexane and ethyl acetate 70:30 ratio to obtain elute 6. Then with a mixture of hexane and ethyl acetate 60:40 ratio to obtain elute 7. Then with a mixture of hexane and ethyl acetate 20:80 ratio to obtain elute 8. Then with 100% ethyl acetate to obtain elute 9.

Figure 5:
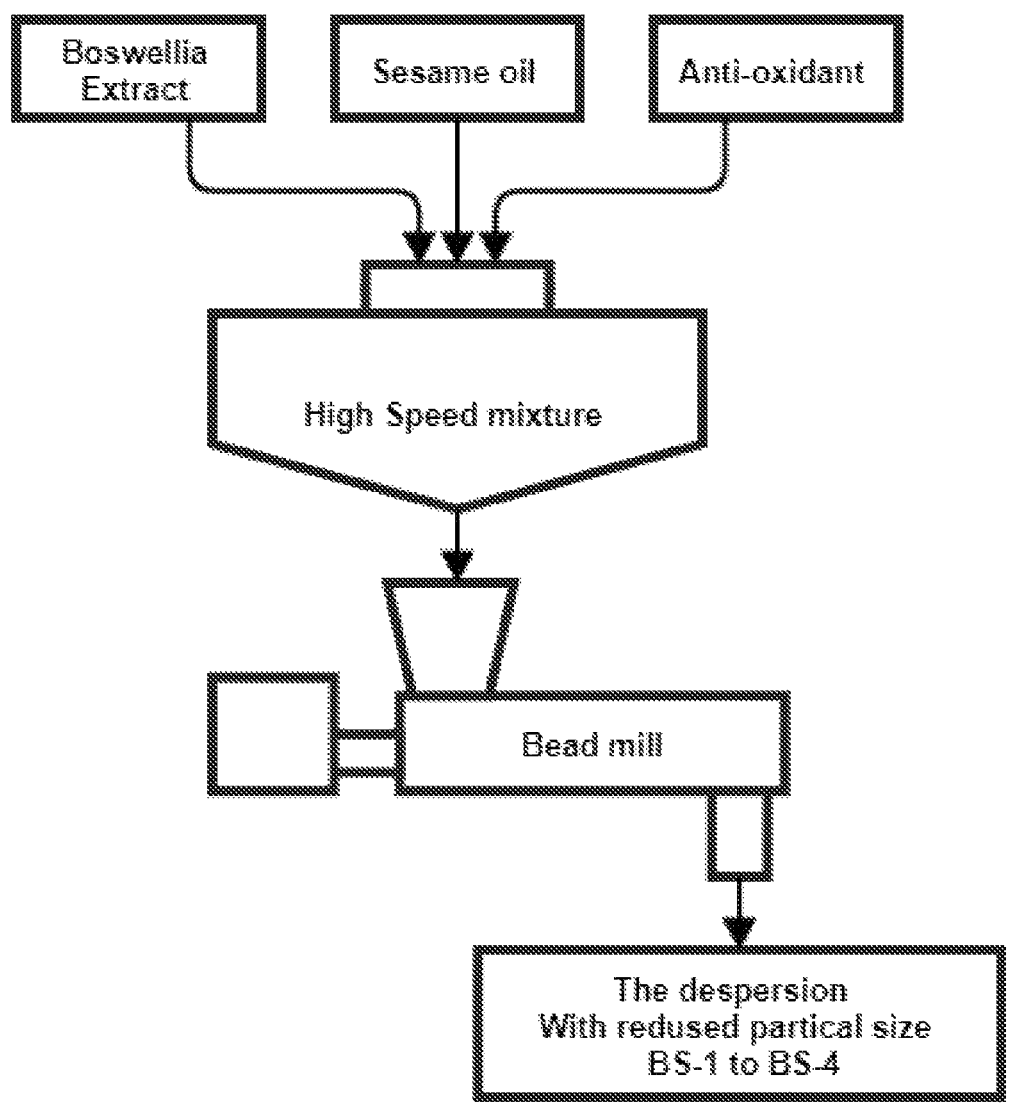
FIG. 5: Method to make *Boswellia* extract dispersion in sesame oil using bead mill.

FIG. 5 A *Boswellia* extracts about 40 Kg, sesame oil 60 Kg and antioxidant about 2000 ppm are taken and they are loaded onto a high speed mixture. The mixture obtained is passed through bead mill to obtain a homogenized mixture. The mixture passed through bead mill once is called BS-1 and the mixture passed twice is called BS-2 and the bead mill passed thrice is called BS-3 and the mixture passed four times is called BS-4.

Figure 6:
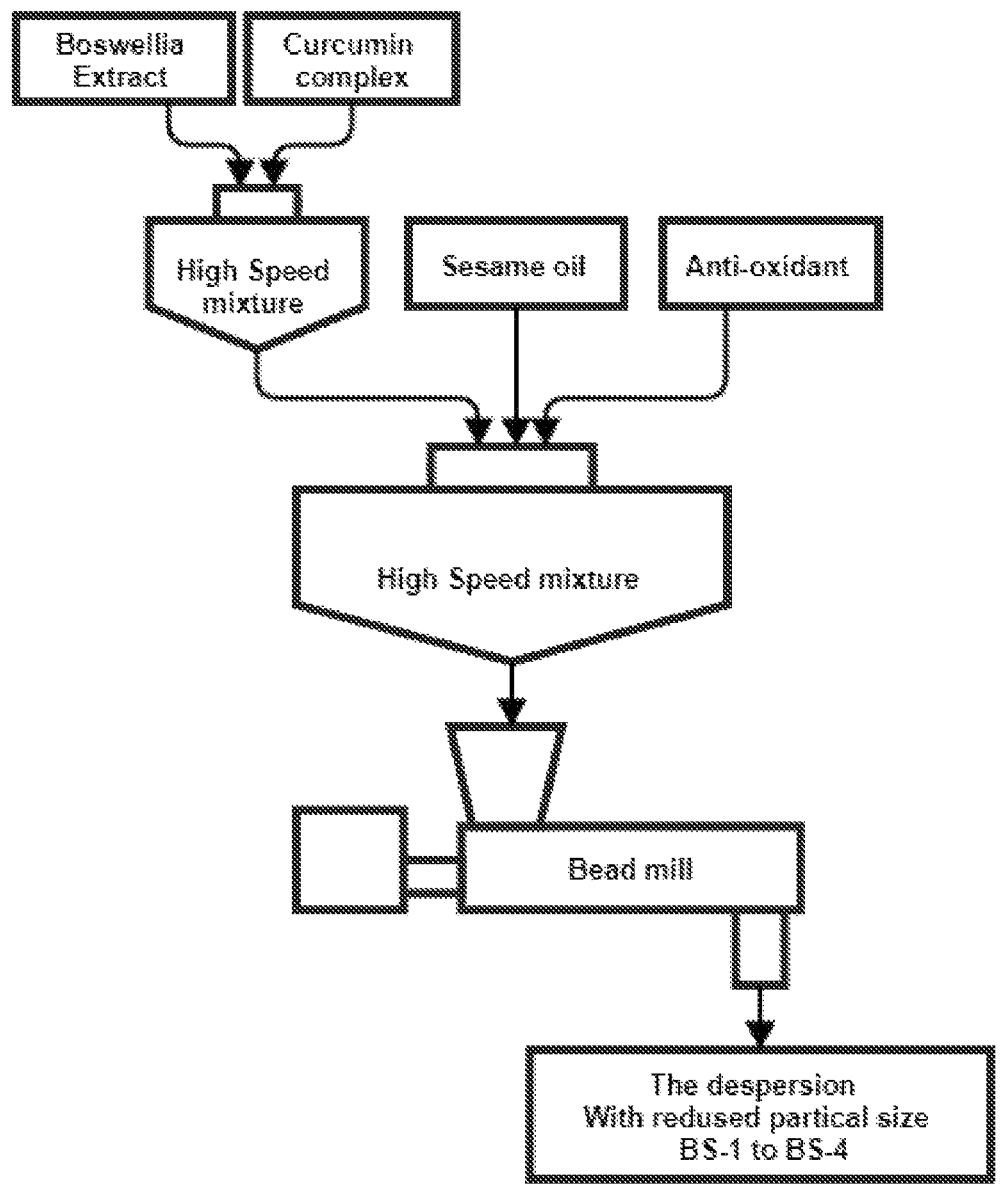
FIG. 6: Method to make *Boswellia* and curcuminoids extract dispersion in sesame oil using bead mill.

FIG. 6 shows a *Boswellia* extract and curcumin composition is mixed in 3:1 ratio. The curcuminoid composition mentioned as curcumin complex in FIG. 6. The 3:1 mixture is taken forward; about 40 Kg of the mixture is mixed with 60 Kg of sesame oil in a high speed mixture. 2000 ppm of antioxidant is also added to the mixture. The mixture from the high speed mixture is taken forward and passed through the bead mill. A homogenized mixture of *Boswellia* extract, curcuminoid composition and sesame oil is obtained from the bead mill.

Figure 7:
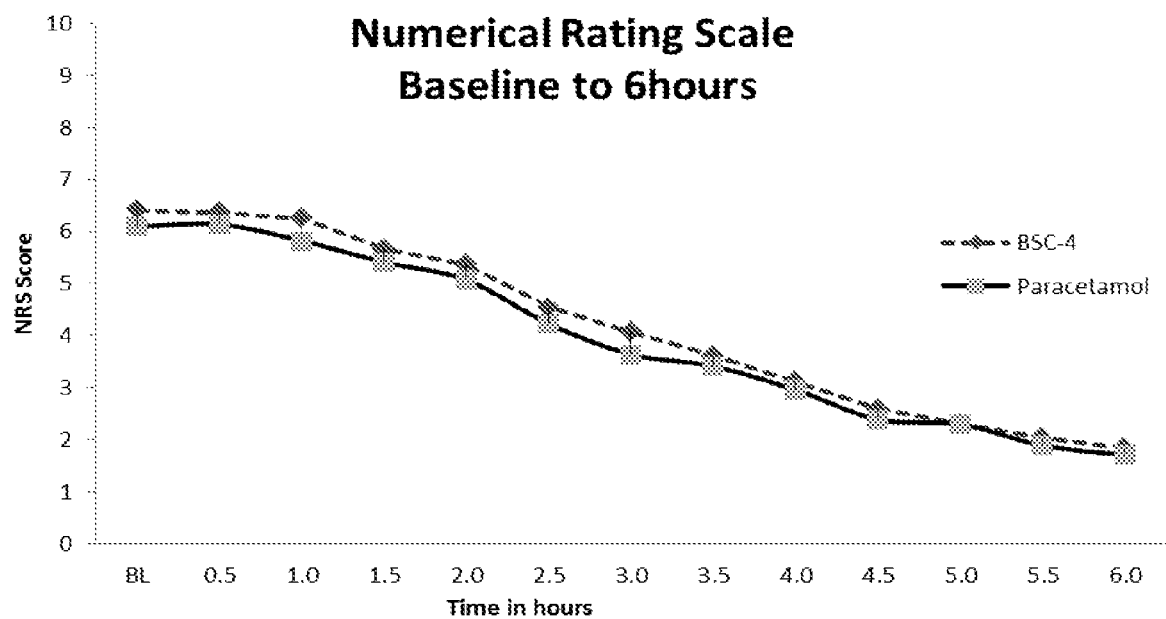
FIG. 7: Graph of Numerical ratting Scale (a) from baseline to six hours and (b) from baseline to 7 days.
Figure 7:
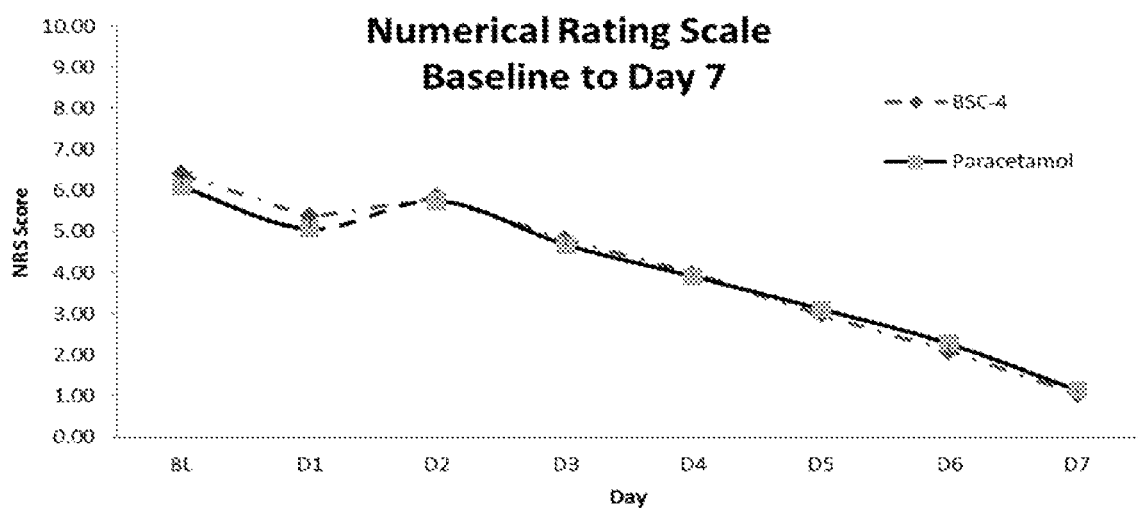

FIG. 7 shows two graphs indicating the change in Numerical Rating Scale (NRS) score with time. Graph (a) indicates the change in NRS score among patients within 6 hours of administration of the drug. The drug administered are BSC-4 and Paracetamol to two different groups of patents. At the baseline the NRS score for patients was around 6. The NRS score went down to 2 for both groups of patents in six hours. In graph (b) indicates the change in NRS score among patients within 7 days of regular use of drug. The base line score in this case was also close to 6, by the end of $7^{th}$ day the NRS score in both groups went done to close to 1.

Figure 8:
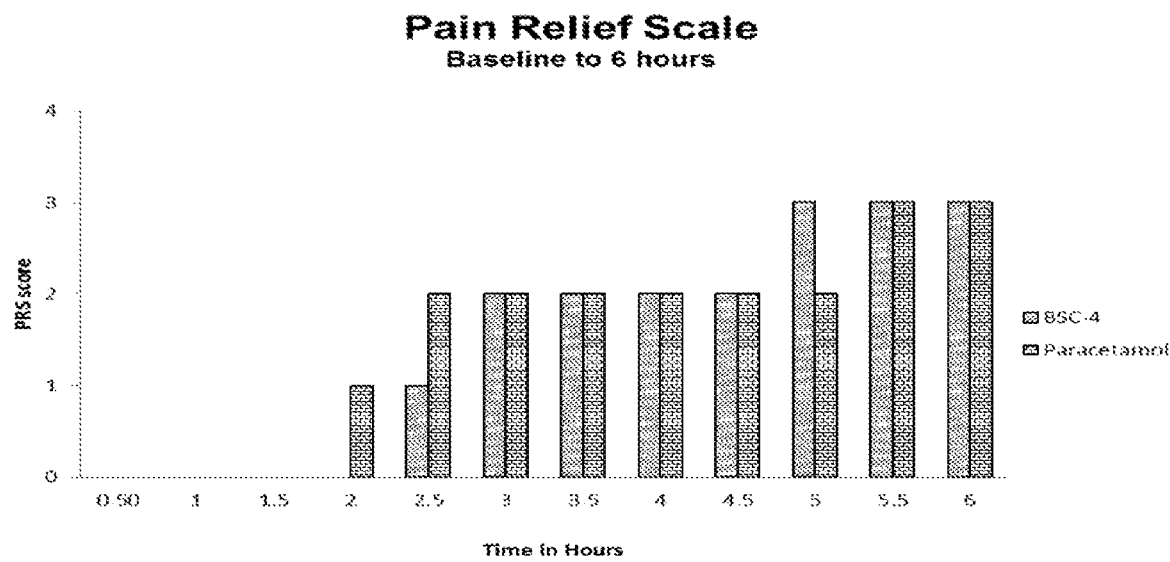
FIG. 8: Graph of Pain relief scale (a) baseline to 6 hours and (b) baseline to 7 days.
Figure 8:
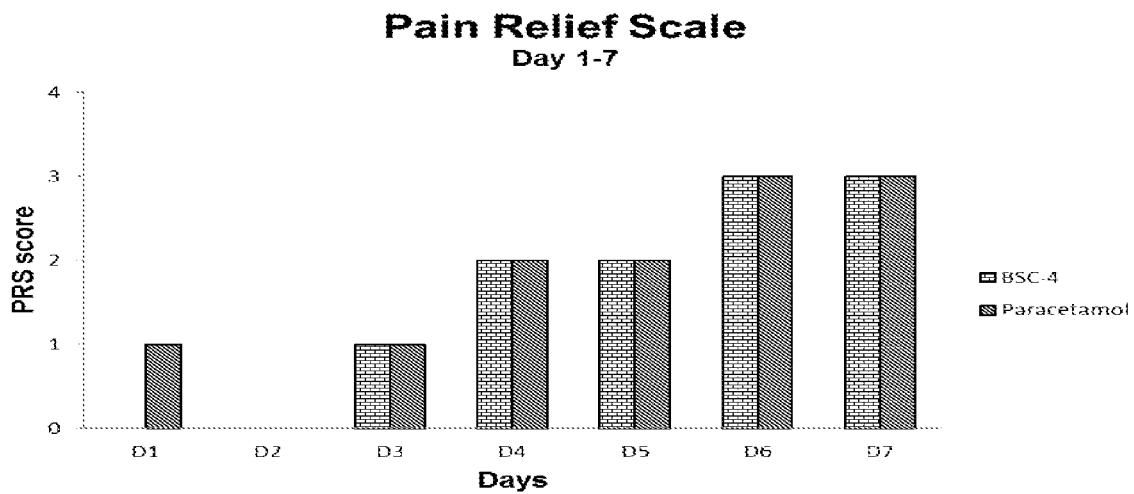

FIG. 8 shows two graphs indicating the change in Pain Relief Scale (PRS) score with time. Graph (a) indicates the change in PRS score among patients within 6 hours of administration of the drug. The drug administered are BSC-4 and Paracetamol to two different groups of patents. At the baseline the PRS score for patients was around 1. The PRS score went up to 3 for both groups of patents in six hours. In graph (b) indicates the change in PRS score among patients within 7 days of regular use of drug. The base line score in this case was close to 1, by the end of $7^{th}$ day the PRS score in both groups went done to close to 3.

Figure 9:
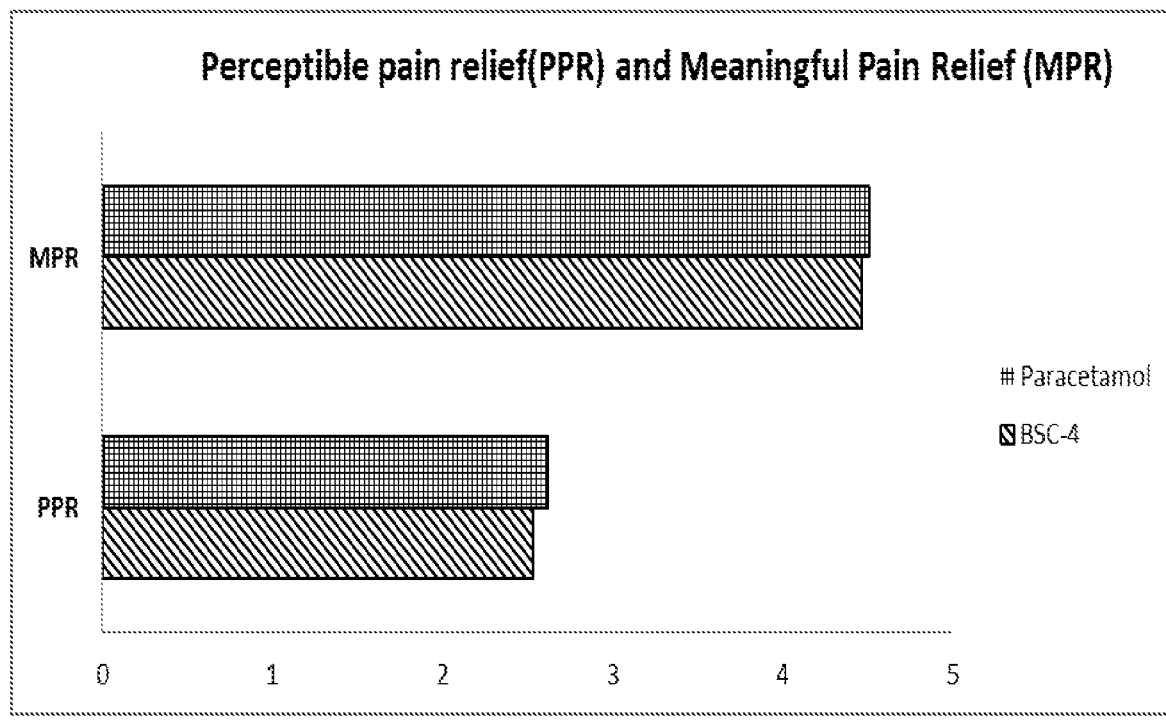
FIG. 9: Graph of Perceptible pain relief and meaning full pain relief.

FIG. 9 shows two graphs indicating the time for perceptible pain relief (PPR) and meaningful pain relief (MPR). The drug administered are BSC-4 and Paracetamol to two different groups of patents. It's a horizontal bar graph first showing the extent of time in each case of PPR and MPR for both groups.

Figure 10:
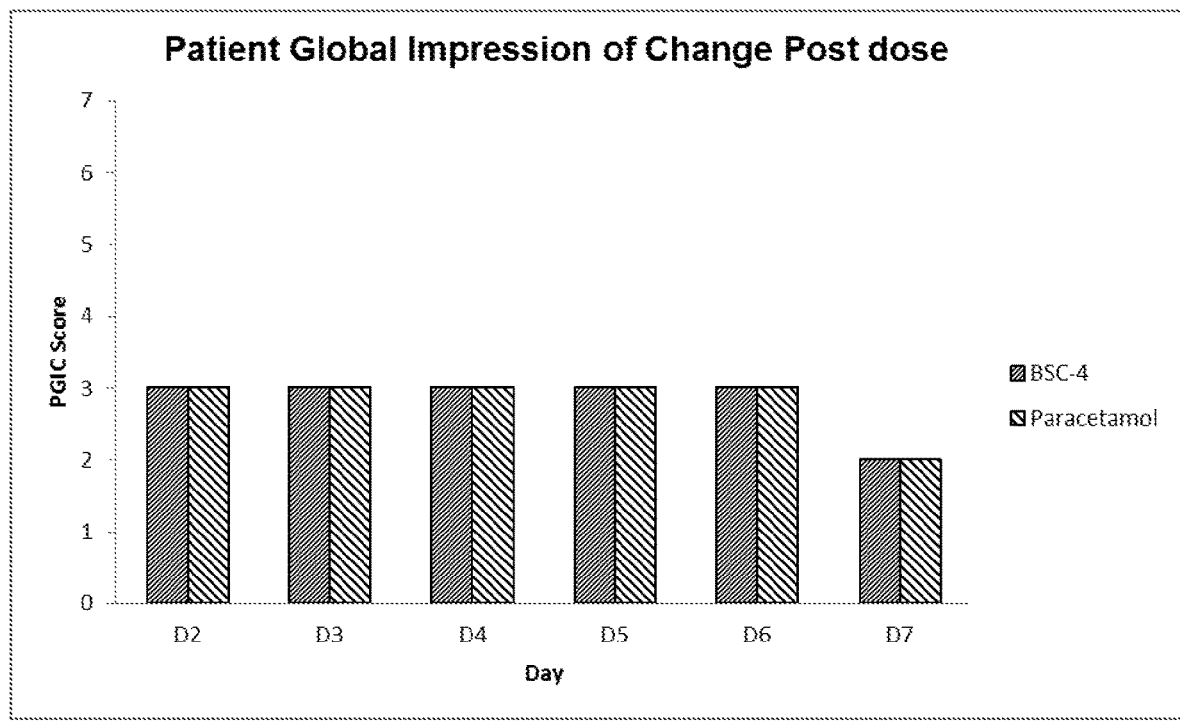
FIG. 10: Graph of Patients Global Impression of Change (PGIC) for seven days.

FIG. 10 shows patients Global Impression of Change Post Dose (GICPD). It's a vertical bar graph showing GICPD of each day till day 7 and for each group of BSC-4 and Paracetamol patents.

The significance of the sesame seed oil blend with Boswellia and curcuminoid composition is illustrated through animal study. The increase in efficacy of plant part when blended with sesame seed oil is illustrated in animal studies provided. Ability to improve bioavailability and activity of sesame seed oil is also illustrated in the examples.

Sesame seed oil is obtained through Sesame seed expeller; it can be cold press or hot press or even solvent extraction. Standard oil has about one percent sesame lignan and if required the lignan can be enriched through column chromatography. For the illustration standard sesame seed oil is used which has about one percent lignans.

The examples disclosed below do not limit the scope of the disclosure.

EXAMPLES

Example 1

The Method to Enrich AKBA to 10% without Alkylation is Described in FIG. 2 and FIG. 3

Boswellia frankincense pellets were used for the extraction. About 1000 Kg of pellets were subjected to steam distillation. The essential oil was collected separately and water used for distillation was drained out from the apparatus, water-soluble part was removed in this way. The residue was dried under vacuum to obtain Sample-1. This was the input material for the process shown in FIG. 3. For Ethyl acetate extraction, a reactor was charged with sample-1, along with double the quantity of Ethyl acetate. The reactor was heated to about 70° C. for about 6 h or till the desired TDS was obtained. The reactor supernatant and residue was formed; the supernatant was filtered out the reactor. The supernatant was cooled to room temperature and a fixed amount of NaOH group was added. The Supernatant was subjected to liquid-liquid extraction with deionized water as another solvent. The Ethyl acetate and water part was separated out and the water part was taken forward. HCL was added to the water part and precipitate was formed. The precipitate was separated out and dried under vacuum. The dried extract was pulverized to get 350 kg of fine powder called as Sample-2.

The fine powdered powder, Sample-2, was the Boswellia extract with 10% [5%] AKBA, 1-3% β-BA, 0.1-0.4% KBA and total boswellic acid was about 35-40% (AKBA10). The final product obtained was immiscible in water. The average SSA of the final powdered extract was less than 120 m$^2$/Kg.

Example 2

The Method of Extracting Boswellia Resin as Shown in FIG. 1 Illustrated.

Boswellia gum resin was used for the extraction. About 1000 Kg of gum resin pellets was loaded into a reactor and was subjected to three times the quantity of hexane for about 5 hours. The hexane part was separated from the residue and oil gets separated along with hexane. The residue was subjected to methanol extraction; two times the quantity of methanol was added into the reactor. The reactor was heated for about 6 h at 70° C., (total dissolved solids) TDS was monitored continuously. A supernatant and residue was formed; supernatant was filtered out and concentrated. The residue was extracted two more times with methanol. All superannuates were collected and concentrated. A powdered methanol extract of Boswellia was obtained, called as sample 3.

The extract, Sample 3, has about 2-4% AKBA, 17-20% β-BA, 4 to 7% KBA and total boswellic acid was about 30-35% (AKBA2). The powdered extract was hydrophobic in nature and had an average SSA of less than 100 m$^2$/Kg. The extract was lipid soluble.

Example 3

Process to Purify AKBA for Boswellia Extract as Described in FIG. 4:

Powder of Boswellia extract from example 2 (sample 3) was mixed with ethyl acetate and blended with silica adsorbent. The ethyl acetate dried off and the silica gel was loaded into a preconditioned silica column. The column was initially eluted with Hexane and Hexane fraction was collected as Elute 1. Then the column was eluted with different ratio of Hexane and Ethyl acetate mixture:

Elute 2—Hx:EA 95:5;
Elute 3—Hx:EA 90:10;
Elute 4—Hx:EA 80:20;
Elute 5—Hx:EA 70:30;
Elute 6—Hx:EA 60:40; and
Elute 7—Hx:EA 20:80.

The column was finally eluted with 100% Ethyl acetate as Elute 8. An elute for each mixture was collected (from Elute 2 to Elute 7), separated and tested for boswellic acids.

The Elute 2 was a mixture of 80% beta boswellic acid and 20% alpha boswellic acid, elute 3 was a mixture of beta-boswellic acid, alpha boswellic acid and 3-O-acetyl boswellic acid, elute 4 was a mixture of, alpha boswellic acid, 3-O-acetyl boswellic acid and acetyl ketoboswellic acid (AKBA), elute 5 was a the mixture of 70% acetyl ketoboswellic acid and 30% ketoboswellic acid, elute 6 was a the mixture of 10% acetyl ketoboswellic acid.

The Elutes were blended in such a manner to get a ratio of E1, E2 and E3;

E1 Elute 5 alone, (AKBA70);
E2—combination of Elute5 and Elute 4 (1:1) (AKBA60);
E3—combination of Elute5 and Elute 4 (1:5). (AKBA50).

Sample 2 or sample 1 could have also been used for this process.

Example 4

Method of Preparing Dispersion of Boswellia in Sesame Oil is Described in FIG. 5.

About 5.6 kg Sesame oil was taken; oil had about 1 to 0.9% sesame lignans. To this, 2000 ppm (of 10 kg) of natural anti-oxidant was added and mixed well. About 4.4 kg Boswellia extract made as per example 1 (sample 2) was weighed and gradually added in the above Sesame oil under continuous mixing in the high-speed mixing vessel to obtain a blend. The blend thus made was passed through a bead mill, in the bead mill the strong inter-movements of grinding media form great shearing, pressing and abrasive force, making the material change shape and generate stress-field. When that stress reaches material breading limit, the material was pulverized. The blend was passed through the bead mill several times. At each pass through the bead mill a sample was collected for study. The samples selected for studies were; BS-1 (200-500 m$^2$/kg) from first pass; BS-2 (700-1000 m$^2$/kg) from second pass, BS-3 (1100-1300 m$^2$/kg) from third pass and BS-4 (>1300 m$^2$/kg) from fourth pass.

The above-said illustration is not limited by the *Boswellia* extract of example 1. But *Boswellia* extract of example 2 and example 3 were also used to make such homogenized blend.

Table below show the composition of the final product (a dispersion).

TABLE 2

| Composition of the dispersion | | | |
|---|---|---|---|
| Sesame oil | 5.6 Kg | sesame lignans | 50 gm |
| *Boswellia* | 4.4 Kg | AKBA | 440 gm |
| | | KBA | 18 gm |
| anti-oxidant | | | 2000 ppm |

Example 5

Method of Making Micron Size Composition of *Boswellia* Acid, Sesame Lignin and Curcuminoid.

About 6 kg Sesame oil was taken as a source of sesame lignans. The sesame oil had 1 to 0.9% sesame lignans. About 3.0 kg *Boswellia* extract made as per example 1 was weighed and gradually added in the above Sesame lignin under continuous mixing in the high-speed mixing vessel. 1.0 kg curcuminoid composition 95% purity extract was weighed and gradually added in the above oil under continuous mixing in the high-speed mixing vessel. To this, 2000 ppm (of 10 kg) of natural anti-oxidant was added and mixed well to obtain a blend. The blend thus made was passed through a bead mill, in the bead mill the strong inter-movements of grinding media form great shearing, pressing and abrasive force, making the material change shape and generate stress-field. When that stress reaches material breading limit, the material was pulverized. The blend was passed through the bead mill several times. At each pass through the bead mill a sample was collected for study.

The samples selected for studies are; BSC-1 (80-100 $m^2$/kg) on first pass; BSC-2 (200-400 $m^2$/kg) on second pass; BSC-3 (600-800 $m^2$/kg) on third pass; and BSC-4 (>900 $m^2$/kg) on forth pass.

Composition of the BSC samples provided in table (a dispersion).

TABLE 3

| Composition of the dispersion | | | |
|---|---|---|---|
| Sesame oil | 6 Kg | sesame lignans | 54 gm |
| *Boswellia* | 3 Kg | AKBA | 300 gm |
| | | KBA | 12 gm |
| Curcuminoid | 1 Kg | Curcuminoids | 884 gm |
| | | Turmeric oil | 70 gm |
| anti-oxidant | | | 2000 ppm |

Example 6

*Boswellia* Extract Simple Blend with Vegetable Oils.

The sample 2 from example one was blended with various vegetable oils in a 2:3 ratio. The blends so made were used as test samples for activity study.

Sample 2 was separated into six batches of 10 Kg each; a, b, c, d, e and f. Each batch was blended with a different oil about 15 Kg each, the oils were selected from a group of sesame seed oil, olive oil, rice bran oil, and coconut oil, cotton seed oil, and *Boswellia* fat. The batch with sample 2 blended with sesame oil was loaded onto a high speed mixture and mixed well to obtain a blend F1. The same process is repeated to obtain F2, F3, F4, F5 and F6.

List of *Boswellia* blend with various oils.

TABLE 4

| F1 | sesame seed oil |
|---|---|
| F2 | olive oil |
| F3 | rice bran oil |
| F4 | coconut oil |
| F5 | cotton seed oil |
| F6 | *boswellia* fat |

Each combination was in a 2:3 ratio of *Boswellia* extract to vegetable oil. As such no uniform mixture was obtained rather a colloid system was formed. The averages SSA of such samples were below 200 $m^2$/kg.

Example 7

Animal Study Comparing Various Blends of *Boswellia* Extract, with Edible Oils for their Anti-Inflammatory Activity.

The animals were housed in polypropylene cages and maintained under standard animal house conditions (12:12 hour light/dark cycle at 24±2° C. and 45-65% relative humidity). The rats had free access to standard pellet diet and water. 24 rats were divided into 8 groups comprising of 3 rats in each group. The rats were deprived of food, but had free access to drinking water for 12 h prior to the experiment. The treatment was as follows:

After 12 hour fasting, baseline paw volume was recorded for each rat using digital plethysmometer (Ugo Basile, Germany). Carrageenan (0.1 ml of 1%) in saline (0.9% NaCl) was injected into the plantar surface of the right hind paw of the animals. The experimental groups were given the designated extract/standard orally, 30 minutes prior to the injection of the carrageenan. After injection of carrageenan, paw volume was recorded at 3 hr. to 6 hr. post carrageenan. The edema was expressed as an increase in the volume of paw from baseline value, and the percentage of inhibition for each rat was calculated.

Each composition of *Boswellia* was obtained through standard mixing of *Boswellia* extract with vegetable oil.

Group 1: 10 mg/Kg Diclofenac.

Group 2: 82 mg/Kg Hydrophobic blend of *Boswellia* extract (10% AKBA) with sesame oil (2:3).

Group 3: 82 mg/Kg Hydrophobic *Boswellia* extract (10% AKBA) with coconut oil (2:3).

Group 4: 82 mg/Kg Hydrophobic *Boswellia* extract (10% AKBA) with olive oil (2:3).

Group 5: 82 mg/Kg Hydrophobic *Boswellia* extract (10% AKBA) with rice bran (2:3).

Group 6: 82 mg/Kg Hydrophobic *Boswellia* extract (10% AKBA) with Cotton seed oil (2:3).

Group 7: 82 mg/Kg Hydrophobic *Boswellia* extract (10% AKBA) with *Boswellia* fat (2:3).

Group 8: 50 mg/Kg Homogenized dispersion hydrophobic *Boswellia* extract with 10% AKBA with sesame oil with 10% sesame lignans. (BS-4).

Percentage inhibition of Inflammation on administration of a mixture of *Boswellia* extract with various oil.

TABLE 5

| Compositions | Rat dose (mg/kg) | Percentage inhibition (%) 3 HR | Percentage inhibition (%) 6 HR | Avrage percentage inhibition |
|---|---|---|---|---|
| Diclofenac | 10 | 66.67 | 69.94 | 68.3 |
| Boswellia extract (10% AKBA) + Sesame oil | 82 | 60.9 | 62.59 | 62 |
| Boswellia extract (10% AKBA) + Coconut oil | 82 | 57.76 | 59.27 | 59 |
| Boswellia extract (10% AKBA) + Olive oil | 82 | 53.33 | 49.33 | 51.33 |
| Boswellia extract (10% AKBA) + Rice bran oil | 82 | 29.29 | 27.36 | 28.32 |
| Boswellia extract (10% AKBA) + Cotton seed oil | 82 | 44.95 | 47.88 | 46 |
| Boswellia extract (10% AKBA) + Boswellia fat | 82 | 37.12 | 41.21 | 39 |
| BS-4 | 50 | 44.48 | 93.4 | 69 |

The results indicate that among all the oil blended with Boswellia extract, it was the sesame oil blend which had the highest activity. Sesame oil was able to enhance the activity of compositions derived from plant parts. Study conducted with other plant part blended with Boswellia oil gave similar results. Sesame oil was able to enhance bioactivity of water insoluble compounds of plants. The blends were also compared with BS-4 which has a much higher efficacy than the other entire blend at a lower dose of 50 mg.

Example 8

Animal Study Comparing Boswellia Extract, Sesame Oil and their Various Combinations for their Anti-Inflammatory Activity.

The animals were housed in polypropylene cages and maintained under standard animal house conditions (12:12 hour light/dark cycle at 24±2° C. and 45-65% relative humidity). The rats had free access to standard pellet diet and water. 42 rats were divided into 9 groups comprising of 3 rats in each group. The rats were deprived of food, but had free access to drinking water for 12 h prior to the experiment. The treatment was as follows:

Group 1: Untreated control.
Group 2: 10 mg/Kg Diclofenac.
Group 3: 20 mg/Kg Hydrophobic Boswellia extract with 2% AKBA (made as per example 2).
Group 4: 20 mg/Kg Hydrophobic Boswellia extract with 10% AKBA (made as per example 1).
Group 5: 30 mg/Kg Sesame seed oil about 0.9% sesame lignans.
Group 6: 50 mg/Kg Simple blend of Boswellia extract with 2% AKBA with Sesame seed oil with 10% sesame lignans (made as per example 6; using AKBA2).
Group 7: 50 mg/Kg Homogenized dispersion of hydrophobic Boswellia extract with 2% AKBA with sesame oil with 10% sesame lignans. (Made as per example 4).
Group 8: 50 mg/Kg Simple hydrophobic Boswellia extract with 10% AKBA with sesame oil with 10% sesame lignans. (Made as per example 6, F1).
Group 9: 50 mg/Kg Homogenized dispersion hydrophobic Boswellia extract with 10% AKBA with sesame oil with 10% sesame lignans. (Made as per example 4).

After 12 hour fasting, baseline paw volume was recorded for each rat using digital plethysmometer (Ugo Basile, Germany). Carrageenan (0.1 ml of 1%) in saline (0.9% NaCl) was injected into the plantar surface of the right hind paw of the animals. The experimental groups were given the designated extract/standard orally, 30 minutes prior to the injection of the carrageenan. After injection of carrageenan, paw volume was recorded at 3 hours to 6 hours post carrageenan. The oedema was expressed as an increase in the volume of paw from baseline value, and the percentage of inhibition for each rat was calculated.

Comparing Boswellia extract, sesame oil and their various combinations for their anti-inflammatory activity.

TABLE 6

| | Groups | percentage inhibition 1 h | 3 h | 5 h | 6 h | Average percentage inhibition |
|---|---|---|---|---|---|---|
| 1 | Untreated control. | NA | NA | NA | NA | NA |
| 2 | 10 mg/Kg Diclofenac. | 64% | 84% | 93% | 97% | 85% |
| 3 | 20 mg/Kg Hydrophobic Boswellia extract with 2% AKBA (SSA < 100 m$^2$/Kg). | 4% | 10% | 7% | 8% | 7% |
| 4 | 20 mg/Kg Hydrophobic Boswellia extract with 10% AKBA. (SSA < 120 m$^2$/Kg). | 17% | 42% | 36% | 42% | 34% |
| 5 | 30 mg/Kg Sesame seed oil with 10% sesame lignans. | 9% | 29% | 28% | 29% | 24% |
| 6 | 50 mg/Kg Simple Blend of Boswellia extract with 2% AKBA with Sesame seed oil with 10% sesame lignans. (SSA < 100 m$^2$/Kg). | 12% | 37% | 38% | 39% | 31.5% |
| 7 | BS-4: 50 mg/kg dispersion of boswellia extract with 2% AKBA in Sesame seed oil with 10% sesame lignans. (SSA > 900 m$^2$/Kg). | 22% | 62% | 65% | 71% | 55% |
| 8 | 50 mg/Kg Simple Hydrophobic Boswellia extract with 10% AKBA with sesame oil with 10% lignans. (SSA < 120 m$^2$/Kg). | 25% | 68% | 69% | 72% | 58.67% |
| 9 | BS-4: 50 mg/Kg dispersion of Boswellia extract with 10% AKBA in sesame oil with 10% Lignans. (SSA > 900 m$^2$/Kg). | 44% | 64% | 81% | 94% | 70.86% |

It was observed that the simple blend of *Boswellia* extract with sesame oil did not show any increase in efficacy, but the inhibition in inflammation seen in simple blend of group 6 and 8 were more or less close the added effect of group 4 and 5 or group 4 and 5. Group 6 was the counterpart of group 7 and group 8 was the counter part of group 9. The only difference in them was the particle size of *Boswellia* extract. The BS-4 blend of group 7 and 9 with the same quantity of *Boswellia* and sesame oil showed an unexpected improvement in its activity as compared to its counterpart group 6 and 8. Even with the same components at the same dose the homogenized blend had a greater efficacy.

Example 9

Activity of *Boswellia* Dispersion in Different SSA Values.

The animals were housed in polypropylene cages and maintained under standard animal house conditions (12:12 hour light/dark cycle at 24±2° C. and 45-65% relative humidity). The rats had free access to standard pellet diet and water. 15 rats were divided into 5 groups comprising of 3 rats in each group. The rats were deprived of food, but had free access to drinking water for 12 h prior to the experiment. The treatment was as follows:

After 12 hour fasting, baseline paw volume was recorded for each rat using digital plethysmometer (Ugo Basile, Germany). Carrageenan (0.1 ml of 1%) in saline (0.9% NaCl) was injected into the plantar surface of the right hind paw of the animals. The experimental groups were given the designated extract/standard orally, 30 minutes prior to the injection of the carrageenan. After injection of carrageenan, paw volume was recorded at 3 hr to 6 hr post carrageenan. The edema was expressed as an increase in the volume of paw from baseline value, and the percentage of inhibition for each rat was calculated.

Group 1: 50 mg/Kg BS-1 (SSA 200-500 $m^2$/kg).
Group 2: 50 mg/Kg, BS-2 (SSA 700-1000 $m^2$/kg)
Group 3: 50 mg/Kg BS-3 (SSA 1100-1200 $m^2$/kg)
Group 4: 50 mg/Kg BS-4 (SSA>1300 $m^2$/kg)
Group 5: 10 mg/Kg Diclofenac.

Percentage inhibition of Inflammation on administration of a BS composition at different SSA.

TABLE 7

| Compositions | Rat dose (mg/kg) | Percentage inhibition (%) 3 HR | 6 HR | Avrage percentage inhibition |
|---|---|---|---|---|
| BS-1 (SSA 200-500 $m^2$/kg) | 50 | 24 | 42 | 34 |
| BS-2 (SSA 700-1000 $m^2$/kg) | 50 | 38 | 68 | 53 |
| BS-3 (SSA 1100-1200 $m^2$/kg) | 50 | 48. | 85 | 66.5 |
| BS-4 (SSA > 1300 $m^2$/kg) | 50 | 67 | 94 | 80.5 |
| Diclofenac | 10 | 68 | 94 | 81 |

It was observed that as the SSA was increasing the activity was also increasing but it's not a linear increase, only after the SSA went over 700 $m^2$/kg a significant increase in activity was observed. BS-1 activities were similar to that of a simple blend of *Boswellia* extract with sesame oil. BS-2, BS-3 and BS-4 are significantly active compared to their standard counterpart, which was just a *Boswellia* blend with sesame oil. The increased surface area enhances the active sites on the *Boswellia* extract which results better molecular linkage between AKBA and sesame lignans. This results in faster absorption and enhanced activity of *Boswellia*.

Example 10

Different Ratios of *Boswellia* and Sesame Oil to Test their Activity.

The animals were housed in polypropylene cages and maintained under standard animal house conditions (12:12 hour light/dark cycle at 24±2° C. and 45-65% relative humidity). The rats had free access to standard pellet diet and water. 27 rats were divided into 9 groups comprising of 3 rats in each group. The rats were deprived of food, but had free access to drinking water for 12 h prior to the experiment. The treatment was as follows:

After 12 hour fasting, baseline paw volume was recorded for each rat using digital plethysmometer (Ugo Basile, Germany). Carrageenan (0.1 ml of 1%) in saline (0.9% NaCl) was injected into the plantar surface of the right hind paw of the animals. The experimental groups were given the designated extract/standard orally, 30 minutes prior to the injection of the carrageenan. After injection of carrageenan, paw volume was recorded at 3 hr to 6 hr post carrageenan. The edema was expressed as an increase in the volume of paw from baseline value, and the percentage of inhibition for each rat was calculated.

Different compositions of sesame oil with *Boswellia* was tested to find out the optimum ratio with enhanced activity.

Each composition of *Boswellia* has undergone a regress milling and grinding resulting in SSA of greater than $1.2 \times 10^3$ $m^2$/kg.

Group 1: 50 mg/Kg AKBA10+Sesame oil (2:3).
Group 2: 50 mg/Kg, AKBA10+Sesame oil (5:7).
Group 3: 50 mg/Kg AKBA10+Sesame oil (9:11).
Group 4: 50 mg/Kg AKBA10+Sesame oil (1:3).
Group 5: 50 mg/Kg AKBA10+Sesame oil (1:5).
Group 6: 50 mg/Kg AKBA10+Sesame oil (1:9).
Group 7: 50 mg/Kg AKBA10+Sesame oil (1:1).
Group 8: 50 mg/Kg AKBA10+Sesame oil
Group 9: 10 mg/Kg Diclofenac Percentage inhibition of Inflammation on administration of a Blend of *Boswellia* with sesame oil in different ratio.

TABLE 8

| Compositions | Rat dose (mg/kg) | Percentage inhibition (%) 3 HR | 6 HR | Average percentage inhibition |
|---|---|---|---|---|
| AKBA10 + Sesame oil (2:3) | 65 | 93 | 79 | 65 |
| AKBA10 + Sesame oil (5:7) | 65 | 93 | 79 | 65 |
| AKBA10 + Sesame oil (9:11) | 66 | 92 | 79 | 66 |
| AKBA10 + Sesame oil (1:3) | 64 | 91 | 77.5 | 64 |
| AKBA10 + Sesame oil (1:5) | 63 | 90 | 76.5 | 63 |
| AKBA10 + Sesame oil (1:9) | 61 | 86 | 73.5 | 61 |
| AKBA10 + Sesame oil (1:1) | 65 | 93 | 79 | 65 |
| AKBA10 + Sesame oil | | | | |
| Diclofenac | 10 | 66 | 98 | 82 |

The results indicate that *Boswellia* extract dispersion in sesame oil in the range of 1:1 to 1:9 gives similar results. Among the compositions provided AKBA10 in sesame oil in the ratio of 2:3, 5:7 and 9:11 are the most effect.

Example 11

Evaluation of Anti-Inflammatory Activity of Test Samples in Carrageenan Induced Paw Edema in Rats:

SD rats (M/F) weighing 180-220 gm. were selected for the study. The animals were acclimatized for a period of five days and they were fed with standard pellet diet and water ad libitum. After five days of acclimatization, the rats were deprived of food, but had free access to drinking water for 12 hours prior to the experiment. Right hind paw of each rat was marked at the tibio-tarsal junction and baseline paw volume was determined using a digital plethysmometer (UGO BASILE, ITALY). Rats were divided into different groups keeping 6 rats in each group. Test sample/standard NSAID/vehicle was fed orally at designated dose. After 30 minutes of test sample/standard/vehicle, 0.1 ml carrageenan (1% suspension in 0.9% NaCl) was injected to the animals in subplantar region of the right hind paw. The paw volume was again determined for all the animals at 6 h after carrageenan injection and percentage inhibition was calculated by using following formula:

$$\text{Percentage inhibition} = \frac{(Vt - V0)\text{control} - (Vt - V0)\text{treated}}{(Vt - V0)\text{control}} \times 100$$

Group 1: Untreated group.
Group 2: Diclofenac administered at 10 mg/Kg.
Group 3: Curcuminoid composition: Containing curcuminoids and turmeric oil in 12:1 ratio.
Group 4: *Boswellia* extract with 10% AKBA from example 2.
Group 5: Sesame oil with 0.9% Sesame lignans.
Group 6: *Boswellia* extract and Curcuminoid composition in 3:1 ratio, with SSA of 100-120 $m^2$/Kg.
Group 7: *Boswellia* extract and Curcuminoid composition and Sesame oil in 3:1:6, with a SSA of 100-120 $m^2$/Kg.
Group 8: *Boswellia* extract and Curcuminoid composition and Sesame oil in 3:1:6, with a SSA of more than >900 $m^2$/kg.

Where, Vt—was paw volume at particular time point, V0—was the paw volume at 0 hour (baseline).

TABLE 9

| | Group | Dosage | Percentage inhibition in 6 Hours. |
|---|---|---|---|
| 1 | Untreated control | NA | NA |
| 2 | Diclofenac | 10 mg/Kg | 86% |
| 3 | *Curcuminoid* composition: Containing *curcuminoids* 92.7% and turmeric oil 7.3%. | 10 mg/Kg | 7% |
| 4 | *Boswellia* extract: Containing 10% AKBA. | 30 mg/Kg | 41% |
| 5 | Sesame oil With 0.9% Sesame lignans. | 60 mg/Kg | 20% |
| 6 | *Boswellia* extract and *Curcuminoid* composition in 3:1 ratio. | 40 mg/Kg | 50% |
| 7 | *Boswellia* extract and *Curcuminoid* composition and Sesame oil in 3:1:6, with a SSA of 100 $m^2$/Kg. | 100 mg/Kg | 64% |
| 8 | *Boswellia* extract and *Curcuminoid* composition and Sesame oil in 3:1:6, with a SSA of more than $0.9 \times 10^3$ $m^2$/Kg. | 100 mg/Kg | 96.9% |

The average percentage inhibition in inflammation in carrageenan induced rats is shown in table 8. Among all the groups, the test sample administered to group 8 animals showed the best results. Group 8 showed 32.9 percentage point improvement over group 7 results, although the composition of sample administered in group 7 and group 8 animals were same. The difference between the sample administered in group 7 and group 8 was the SSA, SSA of sample administered in group 8 was grater that $0.9 \times 10^3$ $m^2$/Kg, whereas the SSA of sample administered to group 7 animals was about 100 $m^2$/Kg.

Test sample administered in group 8 was made of *Boswellia* extract, curcuminoid compound and sesame oil. The individual activity *Boswellia* extract, curcuminoid compound and sesame oil towards inflammation was provided in group 3, 4 and 5. The sum of the activity of group 3, 4 and 5 was close to 68% (7%+41%+20%), whereas the percentage inhibition observed in group 8 was 96.9% that was 28.9 percentage points grater.

It can be concluded that the increase in SSA has enhanced the activity of the *Boswellia* extract, curcuminoid compound and sesame oil combination composition. The activity was significantly greater that the arithmetically predicted value. This unexpected improvement in activity might be the result of the synergy created by enhancing the SSA partials in the composition.

Example 12

Method of Preparation of Essential Oil of Turmeric Enriched with α-Turmerone.

Fresh rhizomes of turmeric (500 Kg) were cleaned. The cleaned turmeric rhizomes were flaked. The flaked turmeric was distilled using water (2500 L) in a vessel. Water was boiled up to 64° C. under stirring condition. Flaked turmeric was added in to the boiled water and stirred for 15 minutes. Then allowed for soaking for 30 minutes. After soaking, the mixture was heated up to 97° C. Distillation started and oil along with water was collected in a separator. Floating oils were collected and contains 30% α-turmerone, 17% Ar-turmerone and 16% β-turmerone.

Example 13

Method of Preparation of Essential Oil of Turmeric with Enriched Ar-Turmerone.

The rhizomes of turmeric (500 Kg) were dried. The dried turmeric rhizomes were powdered to form powdered turmeric. The powdered turmeric was treated with ethyl acetate (1500 L) to form a solution. The extraction was carried out at 78° C. temperature for 1 hr. After initial extraction, the extraction process was repeated 4 more times and the resultant solution was filtered and the solvent was stripped from the filtered solution to form an extract. This extract was cooled to about 4° C. to obtain crystals of curcuminoid mixture (20 Kg) and a liquid. The crystals of curcuminoid were isolated from the liquid by filtration.

The remaining liquid included the essential oil of turmeric and a resin. The liquid was then steam distilled to isolate essential oil of turmeric with 10-15% Ar-turmerone (25 Kg) and alpha turmerone about 4%. Through fractionation the purity of Ar-turmerone can be raised to over 45%.

Example 14

Method of Preparing Turmeric Extract.

The rhizomes of turmeric (300 Kg) were dried. The dried turmeric rhizomes were powdered to form powdered turmeric. The powdered turmeric was treated with ethyl acetate (900 L) to form a solution. The extraction was carried out at 78° C. temperature for 1 hr. After initial extraction, the extraction process was repeated 4 more times and the resultant solution was filtered and the solvent was stripped from the filtered solution to form an extract. This extract was cooled to about 4° C. to obtain crystals of curcuminoid (12 Kg) and a liquid. The crystals of curcuminoid were isolated from the liquid by filtration. The crystals included a mixture of curcumin, demethoxycurcumin and bisdemethoxycurcumin. 95% of the crystals were composed of the mixture of curcumin, demethoxycurcumin and bisdemthoxycurcumin. The crystals were powdered to form powdered curcuminoid mixture. The powdered curcuminoid mixture was also referred to as regular turmeric extract.

Example 15

Method to Prepare Curcuminoid Composition.

The curcuminoid powder prepared as per Example 14 (4.2 Kg) was suspended in water (15 L) to form a suspension. Fraction of essential oil containing Ar-turmerone prepared as per Example 13 (0.35 Kg) was added to the suspension in 12:1 ratio. The mixture was pulverized in a colloidal mill to form fine slurry. Water was stripped from the slurry under heat and vacuum to form a uniform blend (4.55 Kg) having curcuminoid mixture and essential oil containing Ar-turmerone.

Example 16

A Randomized Active Controlled Study to Assess the Efficacy of Sesame Oil Loaded with *Boswellia* Extract and Curcuminoid Composition (BSC-4) in Adult Patients with Acute Musculoskeletal Pain.

Sample size for the study: 88 Subjects were randomized with 1:1 ratio of male and female in each group. Subject selection—Subjects were selected from the screening site who were ready to give a voluntary informed consent and who meets study inclusion criteria.

Inclusion Criteria
1. Adult patient, Male or female between 18-65 years of age.
2. A score of 5 or above on the Numerical Rating Scale.
3. Patients having acute musculoskeletal pain which occurred within 24 hours before presentation e.g. headache musculoskeletal injuries, myalgia, neck pain, limb pain, low back pain, joint pain, widespread musculoskeletal pain, painful uncomplicated acute soft tissue injury of the upper or lower extremity, including acute injuries of ligaments, tendons, or muscles (including Grade 1), not requiring admittance to hospital.
4. Willing to give voluntary informed consent.

Informed consent—The subjects were given the information sheet and explained in detail about all the aspects of the study. They were given enough time to consider about joining the study and all their questions were answered to their satisfaction. There were no coercion of any sort and only those who sign the consent form voluntarily were taken into the study.

Visit 1, randomization; subject were provided BSC-4 or Paracetamol as per the pre-documented randomization list accessed only by pharmacist. Patients were entering the NRS, PRS, and PGIC in the diary before and after 2 hour of taking the dose. Follow up calls were made over phone for patents compliance to treatment, diary completion. The follow up on day 3 the patient were reminded to bring the diary for review and bottle for IP accountability at the next visit.

Visit 2, Physical examination, vitals, and patient diary were checked. Post dose (2 hours) pain intensity using NRS, pain relief using categorical PRS, and patient's global impression of change (PGIC) were recoded.

Visit 3, next visit on $6^{th}$ day from the visit 1, Patients entered the NRS, PRS, and PGIC in the diary before and after 2 hrs of taking the dose. Follow up calls were made over phone for their compliance to treatment, diary completion. The follow up on day 6 the patient were reminded to bring the diary for review and bottle for IP accountability at the next visit.

Physical examination, vitals, and patient diary were checked. Post dose (2 hours) pain intensity using NRS, pain relief using categorical PRS, and patient's global impression of change (PGIC) were recorded.

Assessment

Numerical Rating Scale for Pain (NRS)

The NRS is an 11-point scales in which 0 represents 'no pain' and 10 represents the worst pain possible. The patient were asked to rate their pain intensity as a number from 0 to 10. Alternatively, for better conception it may be explained as below.

TABLE 10

| Scale | Severity |
|---|---|
| 10 | Worst Pain |
| 9 | Severe |
| 8 | |
| 7 | |
| 6 | Moderate |
| 5 | |
| 4 | |
| 3 | Mild |
| 2 | |
| 1 | |
| 0 | No pain |

The NRS were recorded on screening and those patients who have 5 or above score only were enrolled into the study. After the first dose the patient were give the pain intensity rating every 30 minutes up to 6 hours post dose for calculating SPID 6 hrs. The NRS for each hour in provided in FIG. 7(a). The percentage change in pain is provided in table below.

TABLE 11

| Percentage change in pain intensity at 6 hours | |
|---|---|
| BSC-4 | Paracetamol |
| 71.3 | 72.1 |

The NRS was included in the diary and the patient was required to give the pain intensity every morning before taking the dose and 2 hrs after dose until the end of the study. The average of the recorded data is provided in a graphical form in FIG. 7(b). The average percentage change of patents when they visited the centre on day 3 and day 7 is provided below.

TABLE 12

Percentage change in pain intensity in 7 days

| | BSC-4 | Paracetamol |
|---|---|---|
| day 3 | 23.15 | 24.8 |
| day 7 | 81.28 | 83.62 |

Pain Relief Scale (PRS)

The pain relief scale is a categorical scale having a positive progression from 'No relief' to 'complete relief'.

TABLE 13

| Code | Category |
|---|---|
| 1. | No Relief |
| 2. | A Little Relief |
| 3. | Some Relief |
| 4. | A Lot of Relief |
| 5. | Complete Relief |

After the first dose the patient rated the pain relief every 30 minutes up to 6 hours for the assessment of Total pain relief 6 hours. The average pain relief score for the 6 hours test was recorded and represented in graphical form in FIG. 8(a). The average percentage change in pain relief score after 6 hours was recorded and provided in the table below.

TABLE 14

Percentage change in pain relief at 6 hours

| BSC-4 (n = 44) | Paracetamol (n = 44) |
|---|---|
| >75% (n = 28) | >75% (n = 30) |

The pain relief scale was included in the diary and the patient was required to give the pain relief every morning before taking the dose and 2 hours after dose until the end of the study. The average pain relief score for the seven days test was recorded in diary and represented in graphical form in FIG. 8(b). The average percentage change in pain relief score after 3 days and 7th day was recorded and provided in the table below.

TABLE 15

Percentage change in pain relief

| | BSC-4 (n = 44) | Paracetamol (n = 44) |
|---|---|---|
| Day 3 | >50% (n = 21) | >50% (n = 20) |
| Day 7 | >75% (n = 40) | >75% (n = 37) |

After dosing the two stop watches were given to the patient. The patient had to stop one of the watches when he felt relief from pain. This time was taken as the Time to Perceptible Pain Relief (PPR). The average perceptible pain relief in hour is provided in the table below.

TABLE 16

Perceptible pain relief in hour

| BSC-4 | Paracetamol |
|---|---|
| 2.53 | 2.62 |

The second watch was stopped when the patient felt that an adequate pain relief has been achieved. This time was taken as the Time to Meaningful Pain Relief (MPR). If however, MPR was not reached within 6 hours, it was censored at that time point. The average meaningful pain relief in hours is provided in table below and also depicted in graphical form in FIG. 9.

TABLE 17

Meaningful pain relief in hour

| BSC-4 | Paracetamol |
|---|---|
| 4.46 | 4.51 |

Patients Global Impression of Change (PGIC)

In this scale, the patient was asked to rate his overall status since the beginning of treatment.

TABLE 18

| Count | Category |
|---|---|
| 1. | Very Much Improved |
| 2. | Much Improved |
| 3. | Minimally Improved |
| 4. | No Change |
| 5. | Minimally Worse |
| 6. | Much Worse |
| 7. | Very Much Worse |

PGIC was included in the patient diary and the patient had given the impression of change every morning before taking the dose and 2 hrs after the dose until the end of the study. The PGIC score was recorded in diary every day for seven days and is provided in table below and the data is also showed in FIG. 10.

TABLE 19

| Day | 2 | 3 | 4 | 5 | 6 | 7 |
|---|---|---|---|---|---|---|
| BSC-4 | 3 | 3 | 3 | 3 | 3 | 2 |
| Paracetamol | 3 | 3 | 3 | 3 | 3 | 2 |

Significant improvement in pain was observed in all the parameters tested for both the group of BSC-4 and Paracetamol. The efficacy of BSC-4 was observed to be at par with that of Paracetamol. Not only BSC-4 showed clinically significant results but also demonstrates that it can act as an alternative to Paracetamol for pain.

I claim:

1. An analgesic and anti-inflammatory composition for oral use comprising:
   a dispersion of
      a) a solid extract of *Boswellia* comprising acetyl-11-keto-beta-boswellic acid (AKBA), and
      b) a solid extract of *Curcuma longa* comprising curcuminoids,
   in sesame seed oil,
   wherein the solid extracts are loaded into sesame seed oil in a 1:1 to 1:99 ratio by weight, and the particle size of the solid extracts ranges from less than about 20 micrometers to about 1 micrometer.

2. The analgesic and anti-inflammatory composition of claim 1 comprises a total combined specific surface area provided by particles in the composition, wherein the total combined specific surface area provided by particles in the composition ranges from about 900 meter$^2$ per kilogram to about 3000 meter$^2$ per kilogram of the composition.

3. A dosage form comprising the analgesic and anti-inflammatory composition of claim 1.

4. The dosage form of claim 3, comprising the composition in a human at dose of about 50 mg to about 2000 mg.

5. The dosage form of claim 3, comprising about 50% of the composition having a particle size of less than about 5 micrometer.

6. The dosage form of claim 5, wherein the dosage form is selected from the group consisting of hard gel capsule, soft gel capsule, paste, ointment, infusion, injection, ampoule, solution, suspension, emulsion, oil or cream.

7. The composition of claim 1, wherein a weight ratio of extract of *Boswellia*:extract of *Curcuma longa*:sesame seed oil ranges from about 1:1:1 to about 5:1:99.

8. The analgesic and anti-inflammatory composition of claim 1, wherein the sesame seed oil comprises about 30% to about 70% sesame lignans, and the sesame lignans comprises a weight ratio of sesamin:sesamolin of about 1:1.

9. The composition of claim 1, wherein the extract of *Boswellia* comprises about 1% to about 30% acetyl-11-keto-beta-boswellic acid.

10. The composition of claim 9, wherein the extract of *Boswellia* comprises about 10% acetyl-11-keto-beta-boswellic acid.

11. The composition of claim 1, comprising a curcuminoid mixture and an essential oil of turmeric.

12. The composition of claim 1, comprising 60±5% by weight of the sesame oil.

13. The composition of claim 1, wherein the extract of *Curcuma longa* is standardised with about 95% curcuminoids.

* * * * *